US008538548B2

(12) United States Patent
Shi et al.

(10) Patent No.: US 8,538,548 B2
(45) Date of Patent: Sep. 17, 2013

(54) TECHNIQUES FOR SENSING AND ADJUSTING A COMPLIANCE VOLTAGE IN AN IMPLANTABLE STIMULATOR DEVICE

(75) Inventors: Jess Weigian Shi, Winnetka, CA (US); Yuping He, Northridge, CA (US); Que T. Doan, West Hills, CA (US); David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/446,784

(22) Filed: Apr. 13, 2012

(65) Prior Publication Data
US 2012/0197354 A1    Aug. 2, 2012

Related U.S. Application Data

(63) Continuation of application No. 12/199,312, filed on Aug. 27, 2008, now Pat. No. 8,175,719, which is a continuation of application No. 11/305,898, filed on Dec. 14, 2005, now Pat. No. 7,444,181.

(51) Int. Cl.
*A61N 1/05* (2006.01)

(52) U.S. Cl.
USPC .......................................................... 607/62

(58) Field of Classification Search
USPC .......................................... 607/2, 46, 48, 57
See application file for complete search history.

(56) References Cited

U.S. PATENT DOCUMENTS

| | | | |
|---|---|---|---|
| 3,646,940 A | 3/1972 | Timm et al. | 128/421 |
| 3,724,467 A | 4/1973 | Avery et al. | 128/418 |
| 3,822,708 A | 7/1974 | Zilber | 128/419 R |
| 4,197,850 A | 4/1980 | Schulman | 607/34 |
| 4,231,027 A | 10/1980 | Mann | 340/636.11 |
| 4,232,679 A | 11/1980 | Schulman | 607/33 |
| 4,324,251 A | 4/1982 | Mann | 607/30 |
| 4,532,930 A | 8/1985 | Crosby | 607/57 |
| 4,793,353 A | 12/1988 | Borkan | 128/421 |
| 5,643,330 A | 7/1997 | Holsheimer | 607/46 |
| 5,959,371 A | 9/1999 | Dooley | 307/130 |

(Continued)

FOREIGN PATENT DOCUMENTS

| | | |
|---|---|---|
| WO | 00/00251 | 1/2000 |
| WO | 02/09808 | 2/2002 |

OTHER PUBLICATIONS

U.S. Appl. No. 11/177,503, filed Jul. 8, 2005, Peterson et al.

(Continued)

*Primary Examiner* — Scott Getzow
*Assistant Examiner* — Amanda Patton
(74) *Attorney, Agent, or Firm* — Wong, Cabello, Lutsch, Rutherford & Brucculeri, LLP

(57) ABSTRACT

Disclosed herein are methods and circuitry for monitoring and adjusting a compliance voltage in an implantable stimulator devices to an optimal value that is sufficiently high to allow for proper circuit performance (i.e., sufficient current output), but low enough that power is not needlessly wasted via excessive voltage drops across the current output circuitry. The algorithm measures output voltages across the current source and sink circuitry during at least periods of actual stimulation when both the current sources and sinks are operable, and adjusts the compliance voltage so as to reduce these output voltages to within guard band values preferably indicative for operation in transistor saturation. The output voltages can additionally be monitored during periods between stimulation pulses to improve the accuracy of the measurement, and is further beneficial in that such additional measurements are not perceptible to the patient.

21 Claims, 24 Drawing Sheets

(56) References Cited

U.S. PATENT DOCUMENTS

| | | | |
|---|---|---|---|
| 6,076,018 A | 6/2000 | Sturman | 607/72 |
| 6,181,969 B1 | 1/2001 | Gord | 607/59 |
| 6,185,452 B1 | 2/2001 | Schulman | 604/20 |
| 6,317,628 B1 | 11/2001 | Linder | 600/547 |
| 6,355,990 B1 | 3/2002 | Mitchell | 307/64 |
| 6,516,227 B1 | 2/2003 | Meadows et al. | 607/46 |
| 6,597,950 B2 | 7/2003 | Linder | 607/8 |
| 6,609,029 B1 | 8/2003 | Mann | 607/37 |
| 6,690,974 B2 | 2/2004 | Archer | 607/45 |
| 6,741,892 B1 | 5/2004 | Meadows | 607/116 |
| 6,799,070 B2 | 9/2004 | Wolfe | 607/7 |
| 7,009,313 B1 | 3/2006 | Parramon et al. | 307/85 |
| 7,805,189 B2 | 9/2010 | Stein et al. | 607/2 |
| 7,949,393 B2 | 5/2011 | Varrichio et al. | 607/72 |

OTHER PUBLICATIONS

Document # IPCOM000016848D, published at www.ip.com (Jul. 18, 2003).

Document # IPCOM000007552D, published at www.ip.com (Apr. 4, 2002).

M. Ghovanloo, et al.; "A Compact Large Voltage-Compliance High Output-Impedance Programmable Current Source for Implantable Microstimulators;" IEEE Transactions on Biomedical Engineering; vol. 52; No. 1; Jan. 2005.

M. Sivaprakasam, et al.; "A Variable Range Bi-Phasic Current Stimulus Driver Circuitry for an Implantable Retinal Prosthetic Device;" IEEE Journal of Solid-State Circuits; vol. 40; No. 3; Mar. 2005.

A. Uranga, et al.; "Special Section on Functional Electrical Stimulation: An Integrated Implantable Electrical Sacral Root Stimulator for Bladder Control;" International Neuromodulation Society; Neuromodulation, vol. 5; No. 4; 2002.

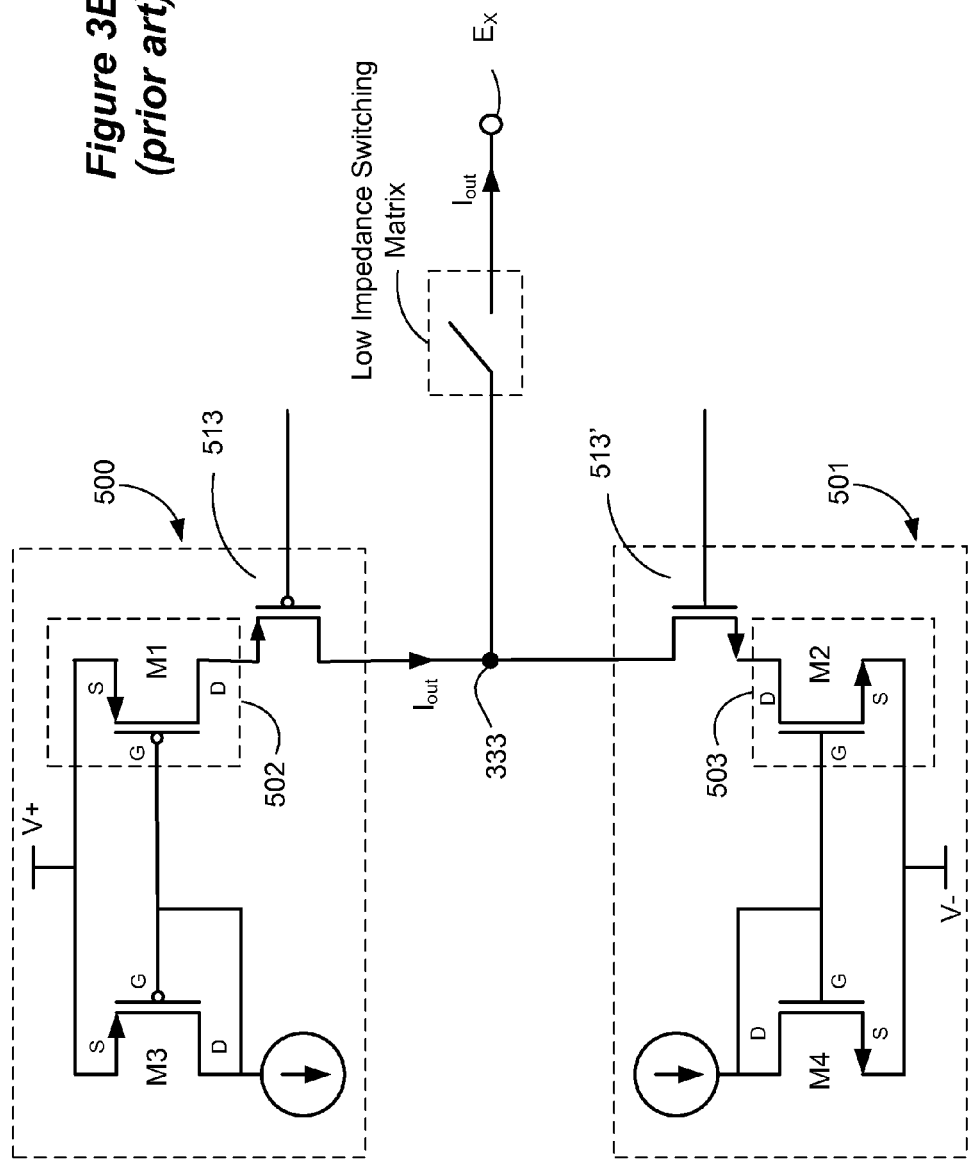

| Chan. | E1 | E2 | E3 | E4 | E5 | E6 | E7 | E8 | E9 | E10 | E11 | E12 | E13 | E14 | E15 | E16 | case |
|---|---|---|---|---|---|---|---|---|---|---|---|---|---|---|---|---|---|
| A | + |   | − | + | − |   |   |   |   |   |   |   |   |   |   |   |   |
| B |   |   |   | − |   | + |   | − |   |   |   |   |   |   |   |   |   |
| C |   |   |   |   |   |   |   |   |   |   | + | − |   |   | + |   |   |
| D |   | + |   |   |   |   |   | − |   |   |   |   |   |   |   | + |   |

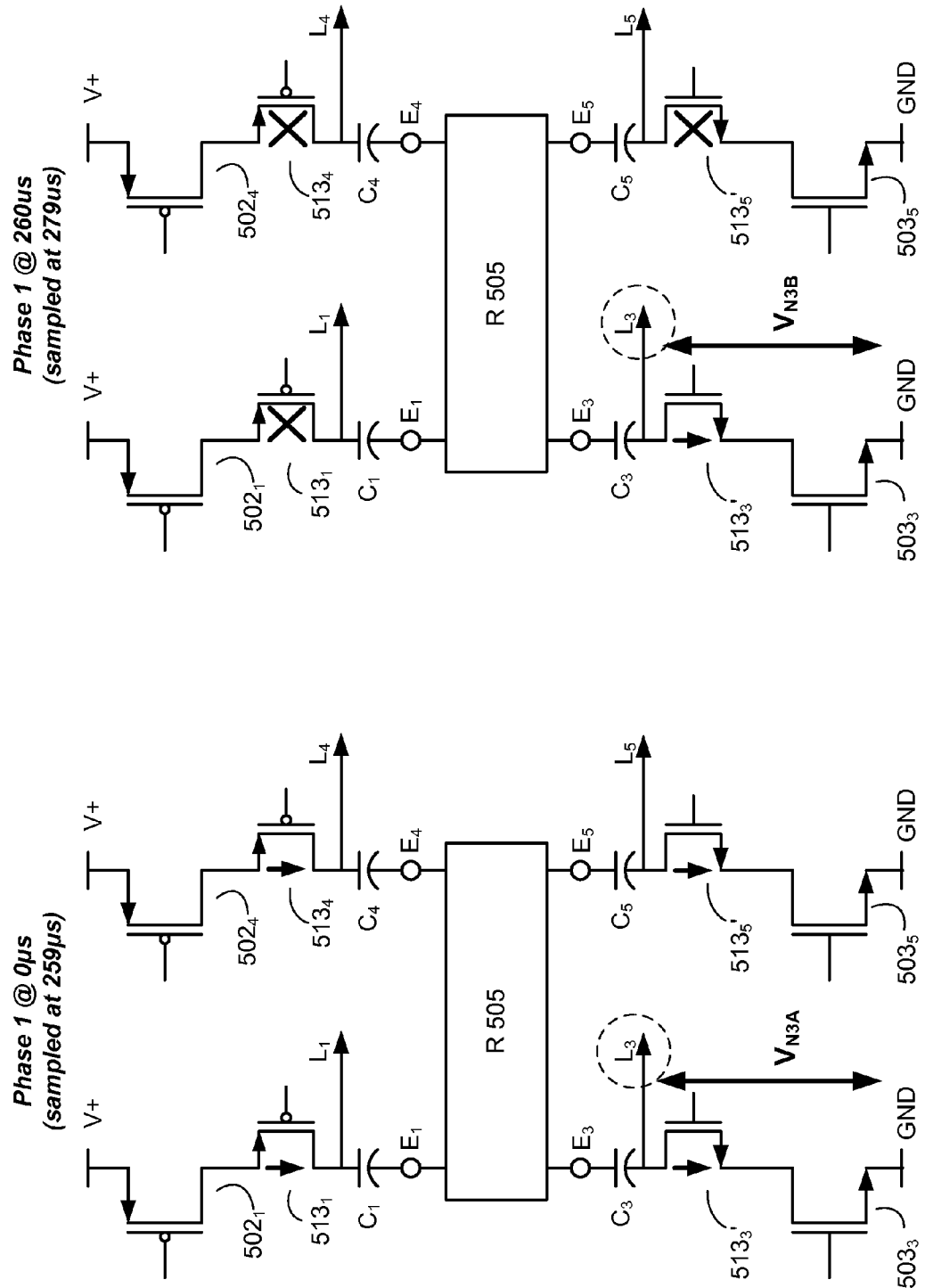

TECHNIQUES FOR SENSING AND ADJUSTING A COMPLIANCE VOLTAGE IN AN IMPLANTABLE STIMULATOR DEVICE

CROSS-REFERENCE TO RELATED APPLICATIONS

This application is a continuation of U.S. patent application Ser. No. 12/199,312, filed Aug. 27, 2008, which was in turn a continuation of U.S. patent application Ser. No. 11/305, 898, filed Dec. 14, 2005 (now U.S. Pat. No. 7,444,181). Priority is claimed to each of these applications, and each is incorporated herein by reference.

FIELD OF THE INVENTION

The present invention relates generally to implantable stimulator devices, e.g., a pulse generator used in a Spinal Cord Stimulation (SCS) system or other type of neural stimulation system. More particularly, the present invention relates to sensing and adjusting a compliance voltage used by the output current source/sink circuitry to ensure proper circuit performance while saving power.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain in certain populations of patients. A Spinal Cord Stimulation (SCS) system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrode contacts (the "electrodes") are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG or RF receiver is implanted. Alternatively, the electrode lead may directly connect with the IPG or RF receiver. For examples of other SCS systems and other stimulation system, see U.S. Pat. Nos. 3,646,940 and 3,822,708, which are hereby incorporated by reference in their entireties. Of course, implantable pulse generators are active devices requiring energy for operation, such as is provided by an implanted battery or an external power source.

An IPG may include one or more output current sources/ sinks that are configured to supply/receive stimulating current to/from the electrodes on the IPG, and ultimately to/from the patient's tissue. For example, FIG. 1 shows a basic output current source 500 and a corresponding output current sink 501 used to stimulate tissue, exemplified generically as a load 505 (R). As one skilled in the art will understand, transistors M1 and M3 in the output current source 500, and transistors M2 and M4 in the output current sink 501, comprise a current mirror. The current mirrors operates to mirror a reference current, $I_{ref}$, in the output stage of the current source or sink, i.e., $I_{out}=I_{ref}$. The reference current $I_{ref}$ can also be scaled by providing paralleled numbers (M) of output transistors (i.e., M1 and M2), such that $I_{out}=M*I_{ref}$. Selection of the various current sources or sinks is typically provided by selection transistors 513 and 513'. As already alluded to, an IPG typically has several electrodes, and the various current sources and sinks can be controlled to source or sink current to any particular electrode, E, as is efficacious for treating a particular patient. As shown in FIG. 1, the current source 500 is connected to IPG electrode $E_X$ while the current sink is connected to electrode $E_Y$.

The output current sources and sinks 500, 501, as one can notice from FIG. 1, are typically formed of transistors of differing polarities. Thus, the sources 500 are formed from P-channel transistors, while the sinks 501 are formed from N-channel transistors. Without a full discussion of transistor physics, one skilled will recognize that use of transistors of such polarities is sensible, given that the sources 500 are typically tied to a positive voltage (V+, referred to herein as the "compliance voltage"), while the sources 501 are typically tied to a more negative voltage, such as ground. (A "ground voltage" as used herein should be understood as any reference voltage with respect to the compliance voltage). (The substrate connection (not shown) for the transistors would typically be tied to the appropriate power supply, either V+ or ground, but could also be tied to the transistors' sources). Because the current sources and sinks 500 and 501 are generally digitally controllable as will be seen (e.g., by transistors 513, 513'), to produce output currents $I_{out}$ of a desired amplitude, such current sources and sinks are typically referred to as Digital-to-Analog Converter circuitry, or "DAC" circuitry. More specifically, in reference to the polarity of the transistors in each, the current sources 500 are typically referred to as "PDACs," while the current sinks 501 are typically referred to as "NDACs."

Different output source/sink architectures can be used in an IPG, and are shown in FIGS. 2-4 respectively. The architecture shown in FIGS. 2A-2B is disclosed in U.S. Pat. No. 6,181,969, which is incorporated herein by reference in its entirety. As shown in FIG. 2A, in the architecture of the '969 patent, each electrode $E_X$ has its own dedicated PDAC and NDAC circuitry, which allows that electrode to either operate as a source of sink of current, or neither. As shown, the PDAC (current source) associated with electrode $E_2$ is active, while the NDAC (current sink) associated with electrode $E_3$ is active, thus producing the current path shown. FIG. 2B shows the PDAC circuitry for a particular electrode usable in the architecture of FIG. 2A. (Only the PDAC circuitry is shown, but one skilled in the art will recognize that the NDAC circuitry for a given electrode would be similarly formed of N-channel devices). As shown, and as one skilled will appreciate, selection transistors 513 are used to digitally set the amplitude of the current to be sourced at electrode $E_X$ (i.e., electrode $E_2$ of FIG. 2A) from $I_{ref}$ to $127I_{ref}$ in increments of $I_{ref}$. As this is explained in detail in the above-incorporated '969 patent, it is not further discussed.

The current architecture of FIGS. 3A-3B is disclosed in above-incorporated U.S. Pat. No. 6,516,227. This architecture is similar to that of FIGS. 2A-2B in that a number of discrete PDAC current source circuitry blocks and NDAC current sink circuitry blocks are provided. However, the PDACs and NDACs are not dedicated to any particular electrode, and instead, each PDAC and NDAC can be coupled to any given electrode via a low-impedance switching matrix, which in reality contains a number of switches to accomplish this task.

Another current sourcing and sinking architecture is disclosed in U.S. patent application Ser. No. 11/177,503, filed Jul. 8, 2005, which is also incorporated herein by reference in its entirety, which is summarized with respect to FIGS. 4A-4C. In this architecture, there is not a discrete plurality of PDAC and NDAC circuit blocks to service the various electrodes. Instead, the current source and sink circuitry is effectively distributed such that they can service any of the electrodes. Thus, a master reference current $I_{ref}$ (which can be scaled from another reference current $I_1$ using a DAC 407 as shown) is used as the input to a number of scalable current mirrors 410 (FIG. 4B). Any one of the current mirrors 410 can be chosen to participate in the current produced at a particular electrode $E_X$ via a switch block 405. Thus, there is a switch block 405 associated with each current mirror 410, in which each switch block has a switch $S_X$ to allow the current from the associated current mirror to be passed to a particular electrode $E_X$.

Regardless of the current source/sink architecture used, all generally have similar current output path characteristics. That is, and referring again to FIG. 1, the current output paths in each architecture comprises, at a minimum, a current source output transistor (or transistors if paralleled for current gain) (M1), a selection transistor to control the flow of the current mirror output transistor(s) (513), the load (R), a current sink mirror transistor or transistors (M2), and a selection transistor to control the flow of the current sink mirror transistor(s) (513'). Each of these elements has some resistance, and hence some amount of the compliance voltage, V+, will be dropped across these elements when current is flowing to stimulate the load, R. Specifically, the compliance voltage V+ will equal $V_{DS1}+V_R+V_{DS2}$, where $V_{DS1}$ comprises the drain-to-source voltage drop across output transistor(s) M1 and selection transistor 513, $V_{DS2}$ comprises the drain-to-source voltage drop across output transistor(s) M2 and selection transistor 513', and $V_R$ equals the voltage drop across the load.

Notice that the M1/M3 and M2/M4 current mirrors require that transistors M1 and M2 operate in a saturation mode, such that the channels of the transistors are in "pinch off." When in saturation mode, the output current $I_{out}$ is proportional to the gate voltage of the transistors M1 or M2, but does not depend upon the drain voltage to the first order. However, to keep the transistors M1 and M2 in the saturation mode, a certain drain-to-source voltage, $V_{DS}$, has to be satisfied for each transistor. Specifically, $V_{DS}$ must be greater than the gate-to-source voltage ($V_{GS}$) minus the threshold voltage ($V_T$) of the transistor (i.e., $V_{DS}>V_{GS}-V_T$). This saturation condition is necessarily satisfied because $V_{DS}=V_{GS}$ by virtue of the common gate/drain connection of transistors M3 and M4. The minimum drain-to-source voltage $V_{DS}$ that satisfies this relationship and allows transistors M1 and M2 to operate in the saturation mode is typically on the order of a volt.

What this means in the context of the output current circuitry of FIG. 1 is that the circuit can operate properly over a range of compliance voltages, V+. For example, suppose a suitable therapy for a patient suggests that a current of $I_{out}=5$ mA should be passed between electrodes $E_X$ and $E_Y$ on the IPG. Suppose further that the load R equals 800 ohms. When the current of 5 mA is passed through the load, a voltage $V_R=4V$ will build up across the load (V=I*R). Suppose further for simplicity that the minimum drain-to-source voltage to keep the output transistors M1 and M2 in saturation equals 1V when the effects of the selection transistors 513, 513' are included. (The actual value can be different, but is chosen as 1V for ease of illustration). To provide this current, a minimum compliance voltage, V+ of at least 6V would be needed; if V+<6V, the circuitry will be unable to produce the desired amount of current.

However, the compliance voltage V+ could be higher than 6V while still producing the proper amount of current. For example, suppose for the same example that the compliance voltage V+ is 8V. In this case, the circuitry is still capable of providing the 5 mA current, and the load (which doesn't change) will still drop 4V at that current. What this means is that the remainder of the compliance voltage must be dropped across the output transistors M1 and M2 as well as their associated selection transistors 513 and 513', e.g., 2V if the source and sink are matched.

However, running the circuit in this example with an 8V compliance voltage is not efficient. While circuit performance is the same at both 6V and 8V, i.e., both are capable of generating a 5 mA current, the former will draw only 30 mW of power (P=I*V), while the latter will draw 40 mW of power. In other words, 10 mW of power are needlessly dropped across the output transistors M1, M2 and their selection transistors 513 and 513'. This waste of power is regrettable in the context of an implantable medical device such as an IPG. As noted earlier, an IPG typically runs from a battery, and therefore it is important to minimize circuit operation that would otherwise needlessly drain the battery and cause the IPG to cease functioning, or needlessly require the patient to more frequently recharge the battery.

Unfortunately, it is difficult to design the compliance voltage to an optimal level. Depending on the electrodes stimulated, the magnitude of current required for efficient therapy for a given patient, and the resistance of the patient's flesh, an optimal compliance voltage from the vantage point of power conservation is variable.

Accordingly, the implantable stimulator art, or more specifically the IPG or SCS system art, would be benefited by techniques for sensing and adjusting the compliance voltage in a manner respectful of the power available to the device. Such solutions are provided herein.

SUMMARY

Disclosed herein are methods and circuitry for compliance voltage sensing and adjustment in an implantable stimulator device. The present invention measures the voltage across (at least) both the output of the PDACs and NDACs involved in sourcing and sinking the stimulation current. Specifically, the voltages across the output transistors of active PDACs and NDACs involved during stimulation (and, preferably, their selection transistors) are measured during actual stimulation, and possibly during inactive periods as well and as discussed further below. These measured voltages are processed in accordance with an algorithm, where they are compared to a range of permissible guard band voltages for both the PDAC and NDAC outputs (e.g., 1.2 to 1.8V for the NDAC outputs, and 1.5 to 2.1V for the PDAC outputs). These guard band voltage ranges comprise a range in which the output transistors are deemed to be properly in saturation, but not excessively so.

Should the measured voltages across the output of the PDAC or NDAC be outside of the guard band voltage, the compliance voltage is changed accordingly to a disclosed algorithm to attempt to bring such measured voltages within acceptable limits while still keeping the NDACs and PDACs balanced. In a preferred embodiment, the compliance voltage V+ starts at a maximum value (e.g., 16.8 V), and the PDAC and NDAC output voltages are measured. V+ is adjusted downward until the minimum voltage across an active NDAC (Min($V_{NX}$)) is below a maximum guard band voltage for the output of the NDACs, e.g., 1.8V. In general, V+ is only decreased until this condition is reached, although the compliance voltage can also be increased slightly (if possible) if Min($V_{NX}$) falls below the minimum guard band voltage (e.g., 1.2V).

Assuming Min($V_{NX}$) is within the NDAC guard band (i.e., between 1.2 and 1.8V), the voltage across the PDACs are similarly measured, and the compliance voltage is potentially further decreased. Thus, if the minimum voltage across an active PDAC (Min($V_{PY}$)) is greater than a maximum guard band voltage for the output transistors of the PDACs, e.g., 2.1V, the compliance voltage is lowered until Min($V_{PY}$) is below 2.1 V. Once Min($V_{PY}$) is within the PDAC guard band (i.e., between 1.5 and 2.1V), the compliance voltage V+ is deemed optimal, as both the output voltage for the PDAC and NDAC are within the guard band voltage, and accordingly are deemed to be in saturation, but not excessively so. However, if Min($V_{PY}$) is below the minimum PDAC guard band value, e.g., 1.5V, V+ can be increased (if possible) and, the compliance voltage V+ is deemed optimal.

During this algorithm, note that V+ can be decreased if Min($V_{PY}$) is above 2.1V, even when Min($V_{NX}$) is below 1.8V and otherwise is optimal. While this would seem to run the risk of adjusting the NDACs out of alignment, note that Min ($V_{NX}$) is tied to (i.e., balanced with) Min($V_{PY}$) by virtue of the current-voltage characteristics of both DACs. Because the currents must match for the NDACs and the PDACs, it is difficult to decrease Min($V_{NX}$) significantly below the minimum NDAC guard band threshold (e.g., 1.2V) without also bringing Min($V_{PY}$) below the minimum PDAC guard band voltage (e.g., 1.5V) and vice versa. Hence, due to this balancing, the compliance voltage can be reduced without significant risk of impacting circuit performance, i.e., such that the circuitry is unable to producing an optimal current.

In a further preferred embodiment, additional NDAC and PDAC output voltages measurements are made during periods in which actual stimulation is not occurring to further improve the accuracy of the compliance voltage adjustment algorithm. Specifically, as well as measuring the output voltages of both the NDACs and the PDACs while active, i.e., during actual stimulation, the output of each specified NDAC and PDAC is also measured while no current is flowing. Thus, the voltage across each NDAC and PDAC is measured during an interphase period, with all other specified NDACs and PDACs disconnected from the circuit via disabling of their selection transistors. This additional non-active, interphase measurement provides an additional output voltage specific for each NDAC and PDAC, which, while generally 0V, may comprise a small voltage (e.g., 0.2V). When this additional measurement is used in the algorithm, the non-active output voltage measurement for a particular NDAC or PDAC is subtracted from the active output voltage measurement for that NDAC or PDAC to arrive at a difference voltage. This difference voltage, which normally would not vary significantly from the active output voltage measurement, is used by the algorithm, and its assessment of voltages within the guard band, etc., to further improve the algorithm's accuracy.

While such non-active measurements are not needed in useful all useful embodiments, and while only active measurements can be used, the non-active measurements, as well as improving accuracy, are beneficial in that they are not taken during periods of stimulation. That is to say, such non-active measurements do not result in significant current flow through the patient. As a result, such non-active measurements are not perceptible by the patient. This is beneficial, because measurements compliance-voltage-optimization measurements preferably do not involve output current stimulation that is not related to conditions deemed necessary for patient therapy. Thus, such additional, non-active measurements can improve the accuracy of compliance voltage adjustment without affecting a therapy regimen prescribed by the IPG.

In short, through the use of the disclosed exemplary algorithm, an optimal compliance voltage taking balancing of the NDACs and PDACs into consideration. The result is sufficient operation of the PDAC and NDAC circuitry, with as low a compliance voltage as possible. As noted above, use of the lowest compliance voltage saves power in the IPG.

BRIEF DESCRIPTION OF THE DRAWINGS

The above and other aspects of the present invention will be more apparent from the following more particular description thereof, presented in conjunction with the following drawings wherein:

FIGS. 3A-3B shows a prior art architecture for coupling output current sources and sinks to a plurality of electrodes using a switching matrix.

FIGS. 15A-18B show activation of the current source/sink circuitry for measuring various output voltages in the current source and sink circuitry in accordance with an embodiment of the invention.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing the compliance voltage sensing and adjustment aspects of the invention, the circuitry, structure, and function of an implantable stimulator device in which the technique can be used is set forth for completeness. The disclosed implantable stimulator device may comprise implantable pulse generator (IPG), or similar electrical stimulator and/or electrical sensor, that may be used as a component of numerous different types of stimulation systems. More specifically, the description that follows relates to use of the invention within a spinal cord stimulation (SCS) system as an exemplary embodiment. However, it is to be understood that the invention is not so limited. Rather, the invention may be used with any type of implantable electrical circuitry that could benefit from improved compliance voltage monitoring and adjustment. For example, the present invention may be used as part of a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover, the technique can be used in non-medical and/or non-implantable devices or systems as well, such as a Transcutaneous Electrical Nerve Stimulator (TENS) device.

Figure 5:
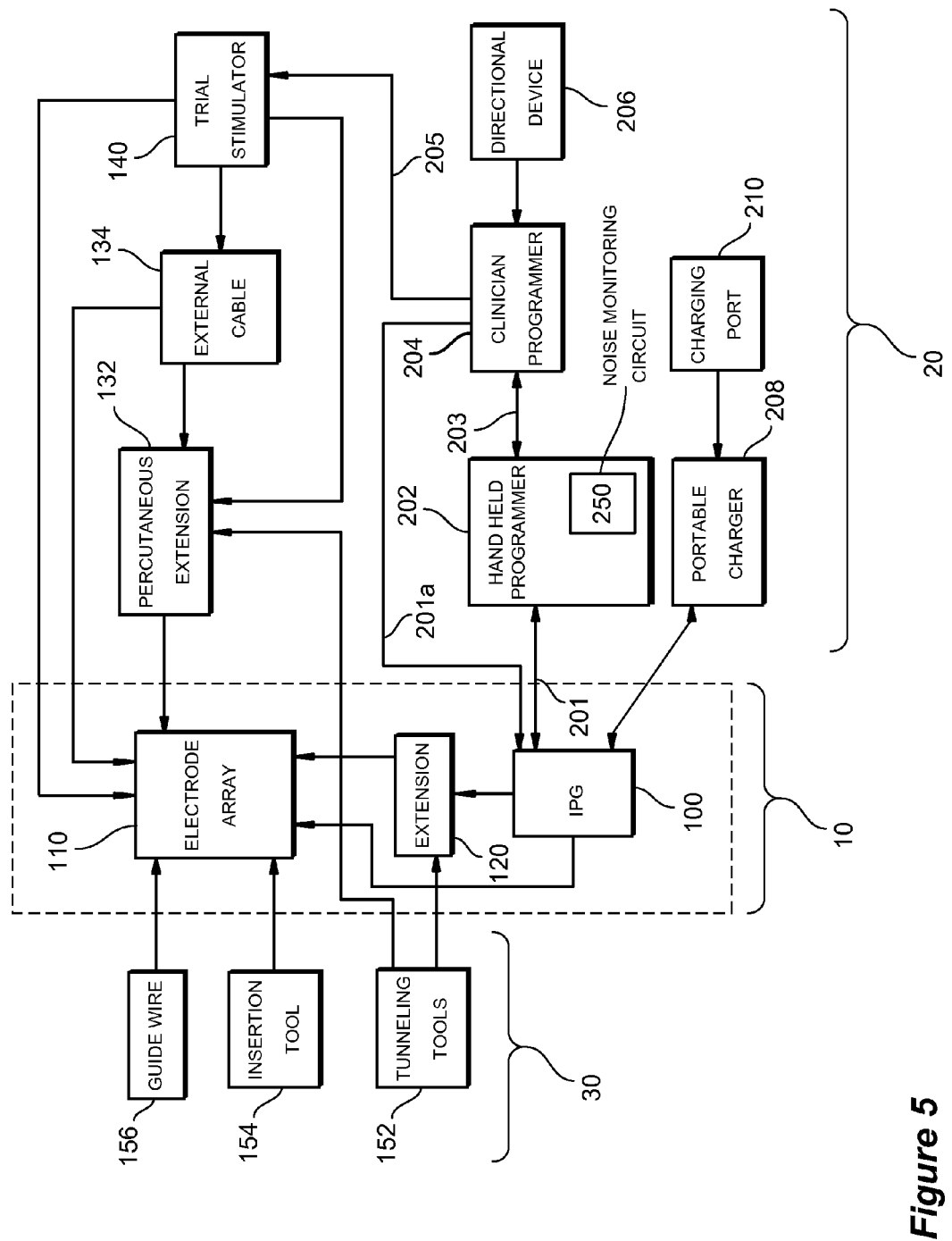
FIG. 5 shows a block diagram that illustrates exemplary implantable, external, and surgical components of a spinal cord stimulation (SCS) system that employs an implantable stimulator device in accordance with the present invention.

Turning first to FIG. 5, a block diagram is shown that illustrates the various components of an exemplary SCS system in which the invention may be used. These components may be subdivided into three broad categories: implantable components 10, external components 20, and surgical components 30. As seen in FIG. 5, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below, may comprise a rechargeable, multi-channel, telemetry-controlled, pulse generator housed in a rounded high-resistivity titanium alloy case 116 (FIG. 7A) to reduce eddy current heating during the inductive charging process. The IPG 100 may provide electrical stimulation through a multiplicity of electrodes, e.g., sixteen electrodes, included within the electrode array 110, as discussed further below with reference to FIGS. 7A and 7B.

Typically, the IPG 100 is placed in a surgically-made pocket either in the abdomen, or just at the top of the buttocks. It may, of course, also be implanted in other locations of the patient's body. Once implanted, the IPG 100 is detachably connected to the lead system, comprising the lead extension 120, if needed, and the electrode array 110. The lead extension 120, for example, may be tunneled up to the spinal column. Once implanted and any trial stimulation period is complete, the lead system 110 and lead extension 120 are intended to be permanent. In contrast, the IPG 100 may be replaced when its power source fails or for other reasons.

Figure 6:
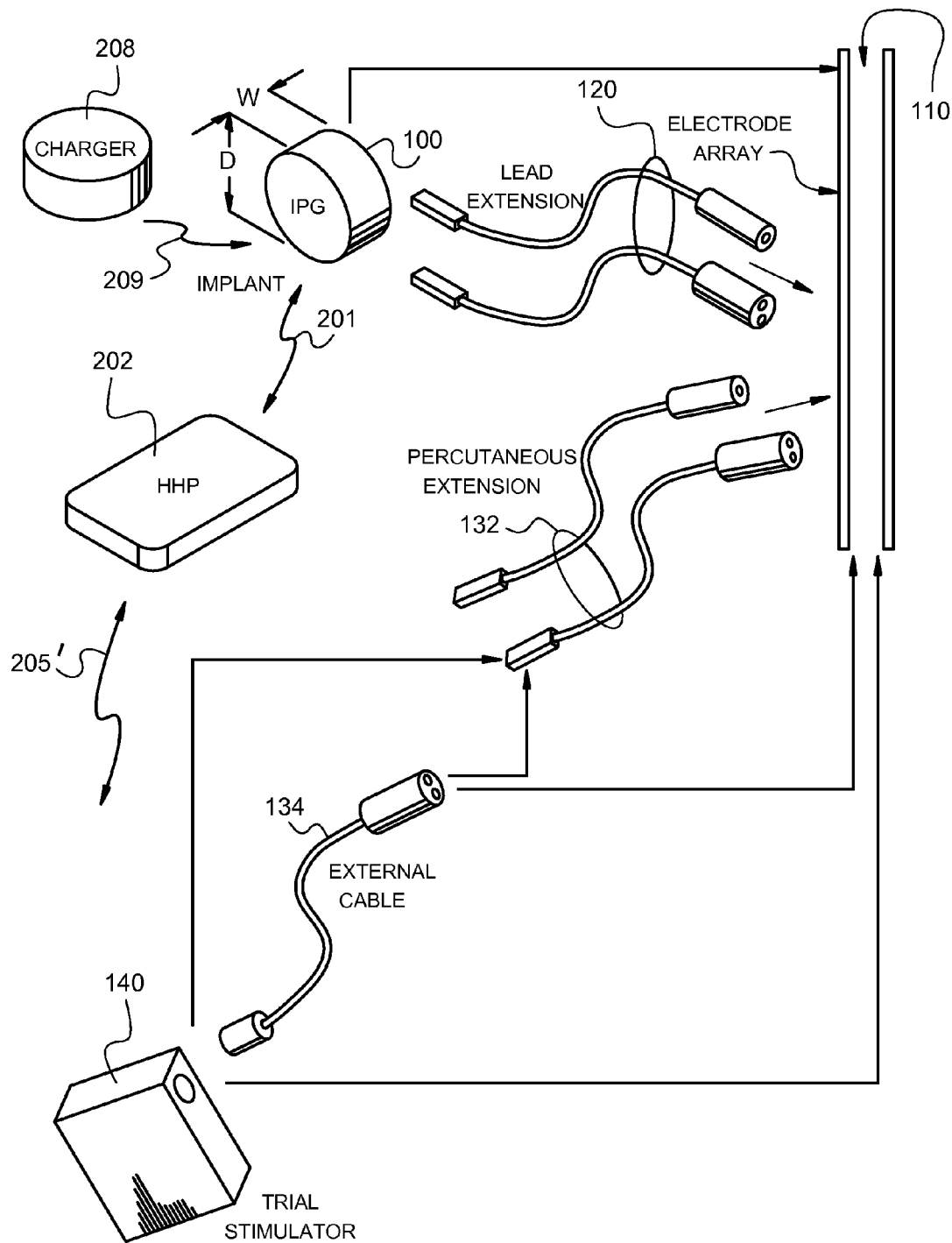
FIG. 6 shows various components of the SCS system of FIG. 5.

As seen best in FIG. 6, and as also illustrated in FIG. 5, the electrode array 110 and its associated lead system typically interface with the implantable pulse generator (IPG) 100 via the lead extension system 120 just mentioned. The electrode array 110 may also be connected to an external trial stimulator 140, through the use of a percutaneous lead extension 132 and/or an external cable 134. The external trial stimulator 140 typically includes the same or similar pulse generation circuitry as does the IPG 100, and is used on a trial basis, e.g., for 7-10 days, after the electrode array has been implanted and prior to implantation of the IPG 100, to test the effectiveness of the stimulation that is to be provided.

Figure 7:
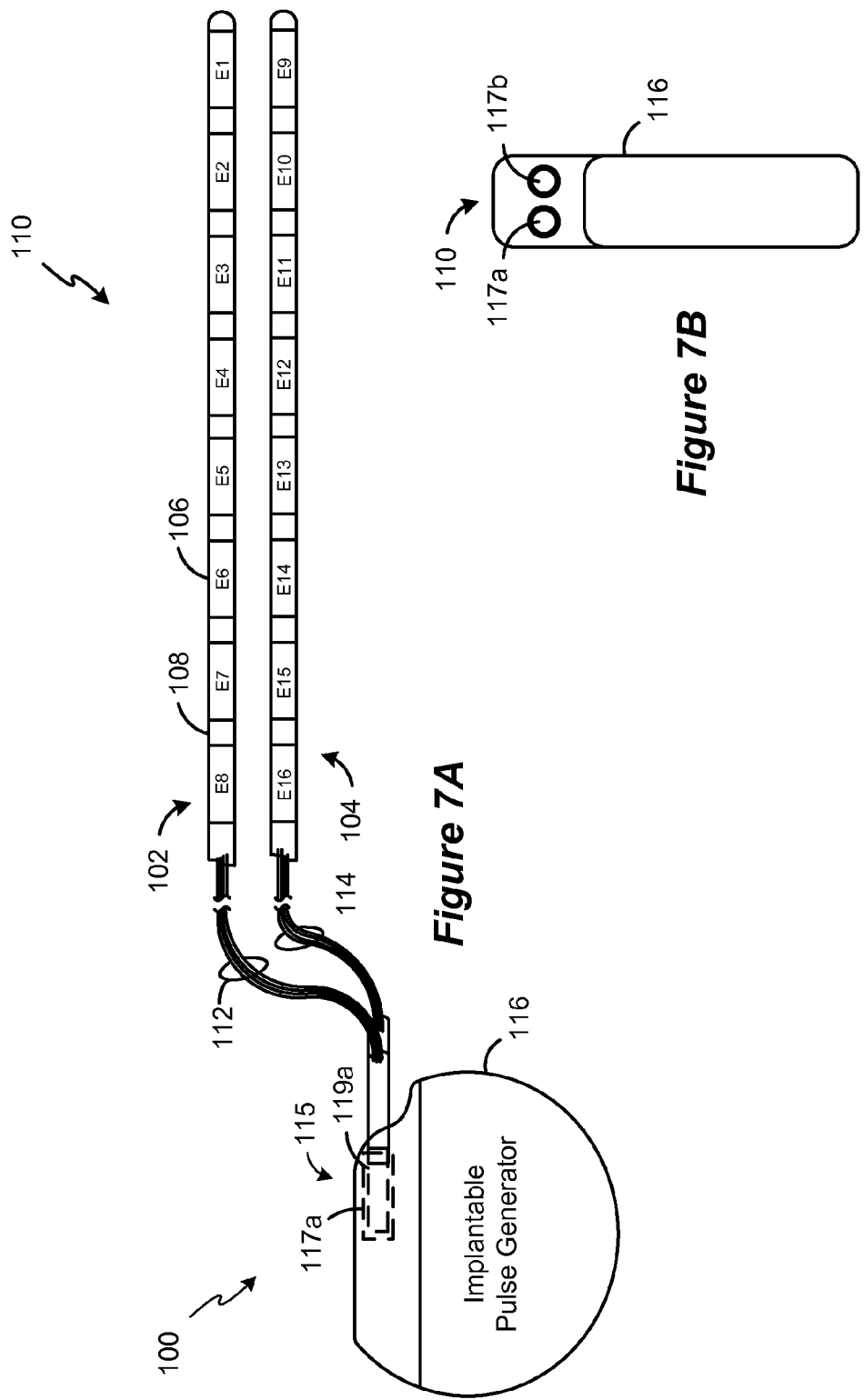
FIGS. 7A and 7B show the electrode array 110 and the manner in which it is coupled to the implantable stimulator device in the SCS system of FIGS. 5 and 6.

FIGS. 7A and 7B show the electrode array 110 and the manner in which it is coupled to the IPG 100. As shown, the electrode array 110 comprises first and second implantable leads 102 and 104. Leads 102 and 104 are in-line leads, meaning that both consist of a plurality of in-line electrodes 106. The electrodes are carried on a flexible body 108. In the illustrated embodiment, there are eight electrodes on lead 102, labeled $E_1$-$E_8$, and eight electrodes on lead 104, labeled $E_9$-$E_{16}$. The actual number of leads and electrodes will, of course, vary according to the intended application and should not be understood in any limiting sense. As discussed above, leads 102 and 104 may be implanted into a desired location, such as adjacent to the patient's spinal column, through the use of an insertion needle or other conventional techniques.

Each of the electrodes 106 on lead 102 are electrically connected to the IPG 100 by a first signal wire 112 that extends through, or is imbedded in, the associated flexible body 108. Similarly, each of the electrodes 106 on the lead 104 are electrically connected to the IPG 100 by second signal wires 114. The signal wires 112 and 114 are connected to the IPG 100 by way of an interface 115. The interface 115 may be any suitable device that allows the leads 102 and 104 (or a lead extension 120, not shown) to be removably connected to the IPG 110. Interface 115 may comprise, for example, an electro-mechanical connector arrangement including lead connectors 117a and 117b (FIG. 7A) configured to mate with corresponding connectors (only connector 119a is shown) on the leads 102 and 104. Alternatively, the leads 102 and 104 can share a single connector that mates with a corresponding connector on the IPG 100. Exemplary connector arrangements are disclosed in U.S. Pat. Nos. 6,609,029 and 6,741,892, which are incorporated herein by reference.

Referring again to FIGS. 5 and 6, and as noted earlier, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set by a patient or clinician within prescribed limits. The HHP 202 may also be linked with the external trial stimulator 140 through another link 205', e.g., an infra red link. Detailed programming of the IPG 100 is preferably accomplished through the use of an external clinician's programmer (CP) 204 (FIG. 5), which may also be hand-held and which may be coupled to the IPG 100 directly via link 201a or indirectly through the HHP 202. An external charger 208, non-invasively coupled with the IPG 100 through link 209, e.g., an inductive link, allows energy stored or otherwise made available to the charger 208 to be coupled into the rechargeable battery housed within the IPG 100.

Figure 8:
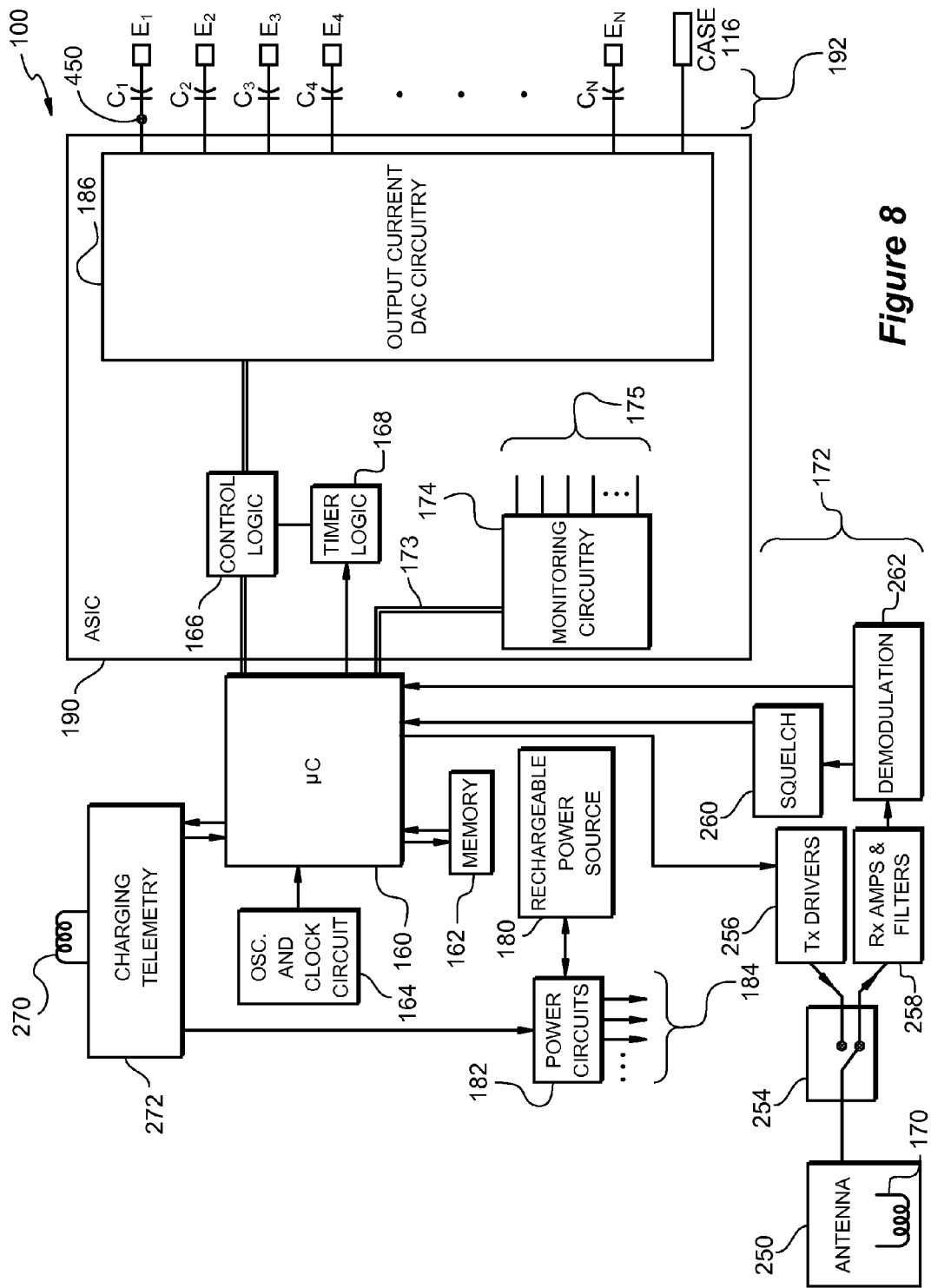
FIG. 8 shows a block diagram that illustrates the main components of one embodiment of an implantable stimulator device in which the invention can be used.

Turning next to FIG. 8, a block diagram is shown that illustrates the main components of one embodiment of an implantable pulse generator (IPG) 100 in which embodiments of the invention may be used. As seen in FIG. 8, the IPG includes a microcontroller (μC) 160 connected to memory circuitry 162. The μC 160 typically comprises a microprocessor and associated logic circuitry, which in combination with control logic circuits 166, timer logic 168, and an oscillator and clock circuit 164, generate the necessary control and status signals to allow the μC 160 to control the operation of the IPG in accordance with a selected operating program and stimulation parameters.

The operating program and stimulation parameters are telemetered to the IPG 100, where they are received via antenna 250 (which may include a coil 170 and/or other antenna components), processed, e.g., via RF-telemetry circuitry 172, and may be stored, e.g., within the memory 162. The RF-telemetry circuitry 172 demodulates the signal it receives from the HHP 202 or CP 204 to recover the operating program and/or the stimulation parameters. More specifically, signals received by the antenna 250 are passed through the transmit/receive switch 254 to amplifiers and filters 258. From there, the received signals are demodulated (262) using Frequency Shift Keying (FSK) demodulation for example, and the data is then sent to the microcontroller 160 for processing and/or eventual storage. When RF-telemetry circuitry 172 is used to transmit information to the HHP 202 or CP 204 to report in some fashion on its status, the microcontroller 160 sends relevant data to transmission drivers 256, where the carrier is modulated by the data and amplified for transmission. The transmit/receive switch 254 would then be set to communicate with the transmission drivers 256, which in turn drive the data to the antenna 250 to be broadcast.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes $E_1 \ldots E_N$, and the like. Informational data sensed through the monitoring circuit 174 may be sent to a remote location external to the IPG (e.g., a non-implanted location) through telemetry circuitry 172 via coil 170. Further details concerning the monitoring circuitry 174 will be discussed later in this disclosure.

The operating power for the IPG 100 may be derived from a rechargeable power source 180, which may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100. In a preferred embodiment, the battery 180 is charged by an electromagnetic field created by an external portable charger 208 (FIG. 5). When placed near the IPG 100 (e.g., centimeters away), an electromagnetic field emanating from the portable charger 208 induces a current in charging coil 270 (even through a patient's skin). This current is then rectified and regulated to charge the battery 180. Further associated with the charging circuitry is charging telemetry circuitry 272, which is used for example by the IPG 100 to report back to the portable charger 208 when the battery is full, and thus when portable charger can be shut off.

In one exemplary embodiment, any of the N electrodes may be assigned to up to k possible groups or "channels." In one preferred embodiment, k may equal four. Moreover, any of the N electrodes can operate, or be included in, any of the k channels. The channel identifies which electrodes are selected to synchronously source or sink current to create an electric field in the tissue to be stimulated. Amplitudes and polarities of electrodes on a channel may vary, e.g., as controlled by the HHP 202 and/or the CP 204.

Figures 11, 12:
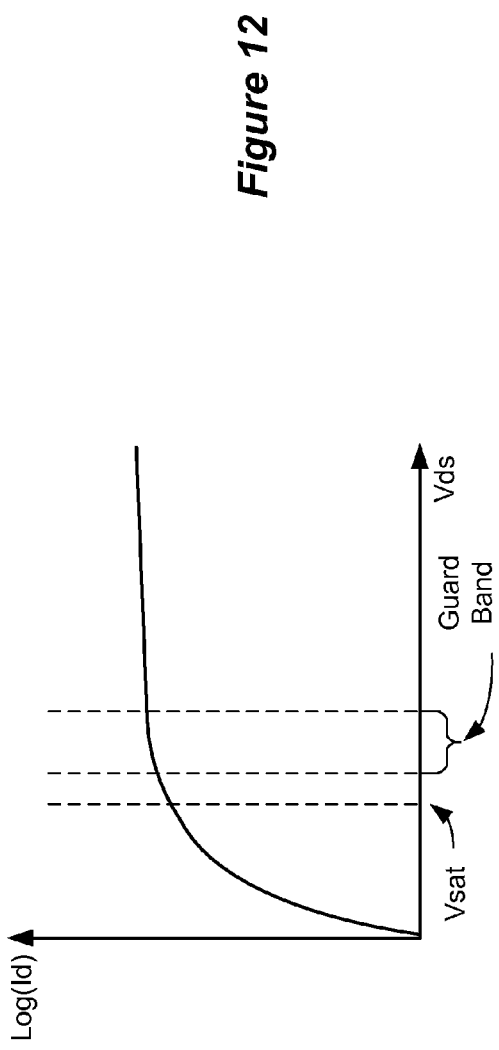
FIG. 11 shows an example of various timing channels usable in an implantable stimulator device, and shows whether each electrode in a channel operates as a source or sink of current.
FIG. 12 shows the I-V characteristics of the output transistors in either the current source or sink circuitry, and shows an optimal guard band voltage range within which the output transistors preferably operate.

For example, as shown in FIG. 11, four channels are defined, and represent groups of electrodes that will be activated as either sources or sinks at a particular time. Thus, in a first timing channel A, electrodes $E_1$ and $E_4$ will act as current sources (denoted by the plus symbol), while electrodes $E_3$ and $E_5$ will act as sinks (denoted by the minus symbol). Electrodes without any designator in FIG. 11 are not activated and do not participate in the sourcing or sinking of current. By designating different channels in this manner, the stimulation provided to the patient can be freely varied with desired therapeutic effect. Note that the case 116 (FIG. 7A) of the IPG 100 can also operate as an electrode which can source or sink current. This allows the IPG to be operated in any number of different modes, e.g., a monopolar mode (one electrode $E_X$ active with an active case), a bipolar mode (two electrodes $E_X$ active), or a multipolar mode (more than two electrodes $E_X$ active).

Ultimately, the grouping of the electrodes into different channels is managed by the control logic 166 (FIG. 8), with the timing of the activation of the various electrodes in each channel being handled by the timer logic 168. The control logic 166, receiving commands from the microcontroller 160, further sets the amplitude of the current pulse being sourced or sunk to or from a given electrode contact. Such current pulse may be programmed to one of several discrete current levels, e.g., between 0 to 10 mA in steps of 0.1 mA. The pulse width of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charge balanced. This means that the amount of positive charge associated with a given stimulus pulse is offset with an equal and opposite negative charge. Charge balance may be achieved through coupling capacitors $C_X$, which provide a passive capacitor discharge that achieves the desired charge-balanced condition. Alternatively, active biphasic or multiphasic pulses with positive and negative phases that are balanced may be used to achieve the needed charge balanced condition.

As shown in FIG. 8, much of circuitry included within the IPG 100 may be realized on a single application specific integrated circuit (ASIC) 190. This allows the overall size of the IPG 100 to be quite small, and readily housed within a suitable hermetically-sealed case 116 (FIG. 7A). The IPG 100 may include feedthroughs to allow electrical contact to be individually made from inside of the hermetically-sealed case with the N electrodes that form part of the lead system outside of the case, as was discussed above with reference to FIG. 7B.

The telemetry features of the IPG 100 allow the status of the IPG to be checked as noted earlier. For example, when the HHP 202 and/or the CP 204 initiate a programming session with the IPG 100 (FIG. 5), the capacity of the battery is telemetered so that the external programmer can calculate the estimated time to recharge. Any changes made to the current stimulus parameters are confirmed through back-telemetry, thereby assuring that such changes have been correctly received and implemented within the implant system. Moreover, upon interrogation by the external programmer, all programmable settings stored within the implant system 10 may be uploaded to one or more external programmers.

Figure 9:
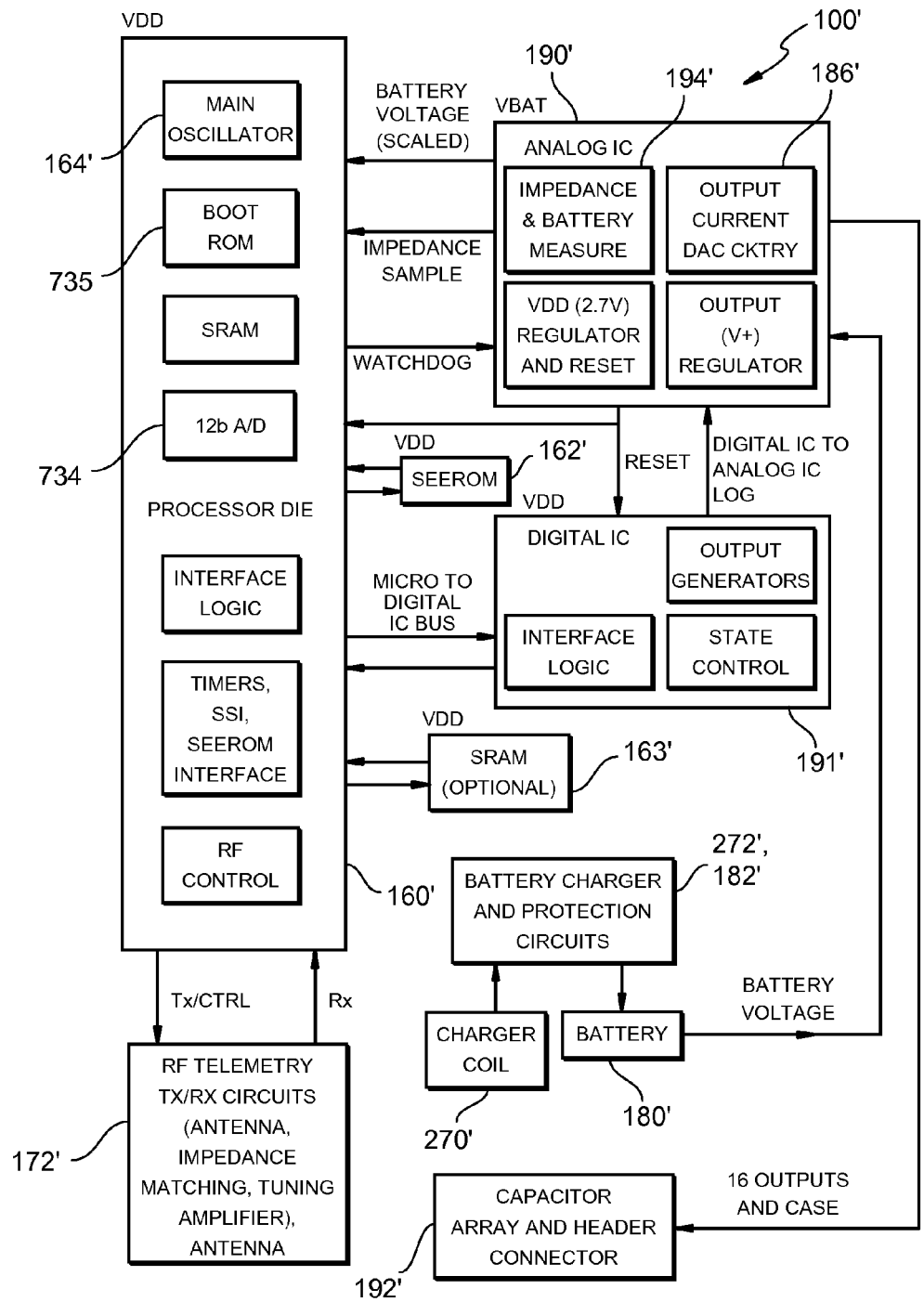
FIG. 9 shows a block diagram that illustrates another embodiment of an implantable stimulator device in which the invention can be used.

Turning next to FIG. 9, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 8. The IPG 100' includes a processor die, or chip, 160', an RF telemetry circuit 172' (typically realized with discrete components), a charger coil 270', a rechargeable battery 180', battery charger and protection circuits 272', 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, SRAM or other memory, two synchronous serial interface circuits, a serial EEPROM interface, and a ROM boot loader 735. The processor die 160' may further include an efficient clock oscillator circuit 164', and (as noted earlier) mixer and modulator/demodulator circuitry implementing the QFAST RF telemetry method. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single channel in 0.1 mA steps. However, it will be noted that the output current DAC circuitry 186' may be configured to deliver any amount of aggregate current and any amount of current on a single channel, according to one exemplary embodiment.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors $C_X$ and electrodes $E_X$, as well as the remaining circuitry on the analog IC 186', may all be housed within the hermetically sealed case of the IPG 100. A feedthrough pin, which is included as part of the header connector 192', allows electrical connection to be made between each of the coupling capacitors $C_N$ and the respective electrodes $E_1$, $E_2$, $E_3$, ..., or $E_{16}$.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

With the basic structure of an implantable stimulator understood, focus now shifts to a detailed description of the compliance voltage sensing and adjustment techniques that are the focus of this disclosure.

Figure 1:
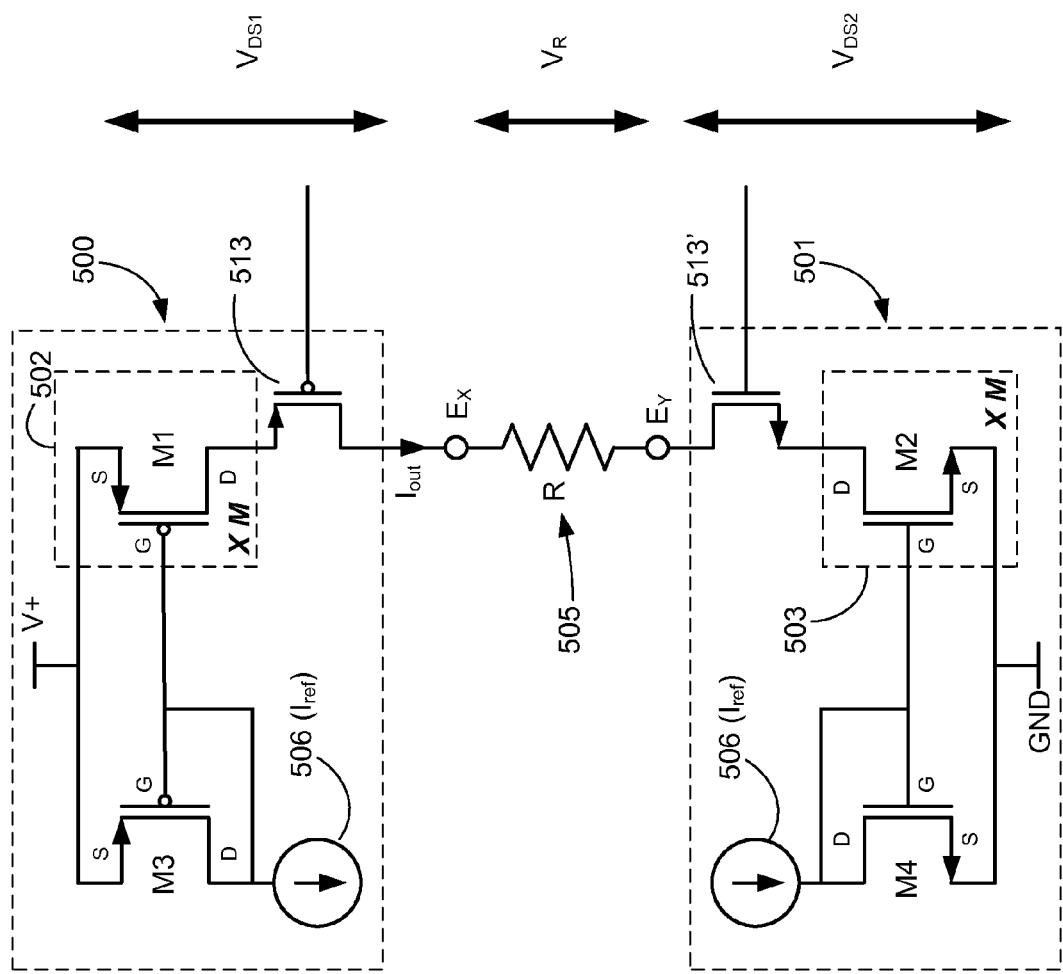
FIG. 1 shows an exemplary output current source and a corresponding output current sink each having current digital-to-analog current (DAC) circuitry in series with a load.

As noted earlier, the compliance voltage, V+, can be set to various values while still exhibiting satisfactory current sourcing/sinking performance. Thus, the NDACs (current sinks) and the PDACs (current sources) involved in stimulation of tissue can be powered by a compliance voltage ranging from a minimum value (below which current will be too low) to any maximum value which the IPG 100 is capable of providing. Within this range, the stimulation current desired by a particular therapeutic regimen can be provided. However, while the compliance voltage V+ can vary over a range of values while exhibiting satisfactory performance, power is needlessly lost should the compliance voltage be set to a value that is too high. Specifically, if the compliance voltage is set too high, the drain-to-source voltage ($V_{DS}$) across the output transistors 502, 503 (FIG. 1) is needlessly increased beyond the saturation values that are required for proper circuit operation. The result, as noted earlier, is needlessly wasted power in the IPG 100, which reduces battery life.

Accordingly, the present invention measures the voltage across (at least) the output of the PDACs and NDACs involved in sourcing and sinking the stimulation current. In a preferred embodiment, the voltage across the PDAC and NDAC selection transistors as well as the PDAC and NDAC output transistors is also included in this measurement, although such additional voltage due to the selection transistors, while significant, may be relatively small. These voltages are measured (at least) during actual stimulation, and are compared to a range of permissible guard band voltages for both the PDAC and NDAC outputs (e.g., 1.2 to 1.8V for the NDAC outputs, and 1.5 to 2.1V for the PDAC outputs). These guard band voltage ranges comprise a range in which the output transistors are deemed to be properly in saturation, but not excessively so.

Figure 10:
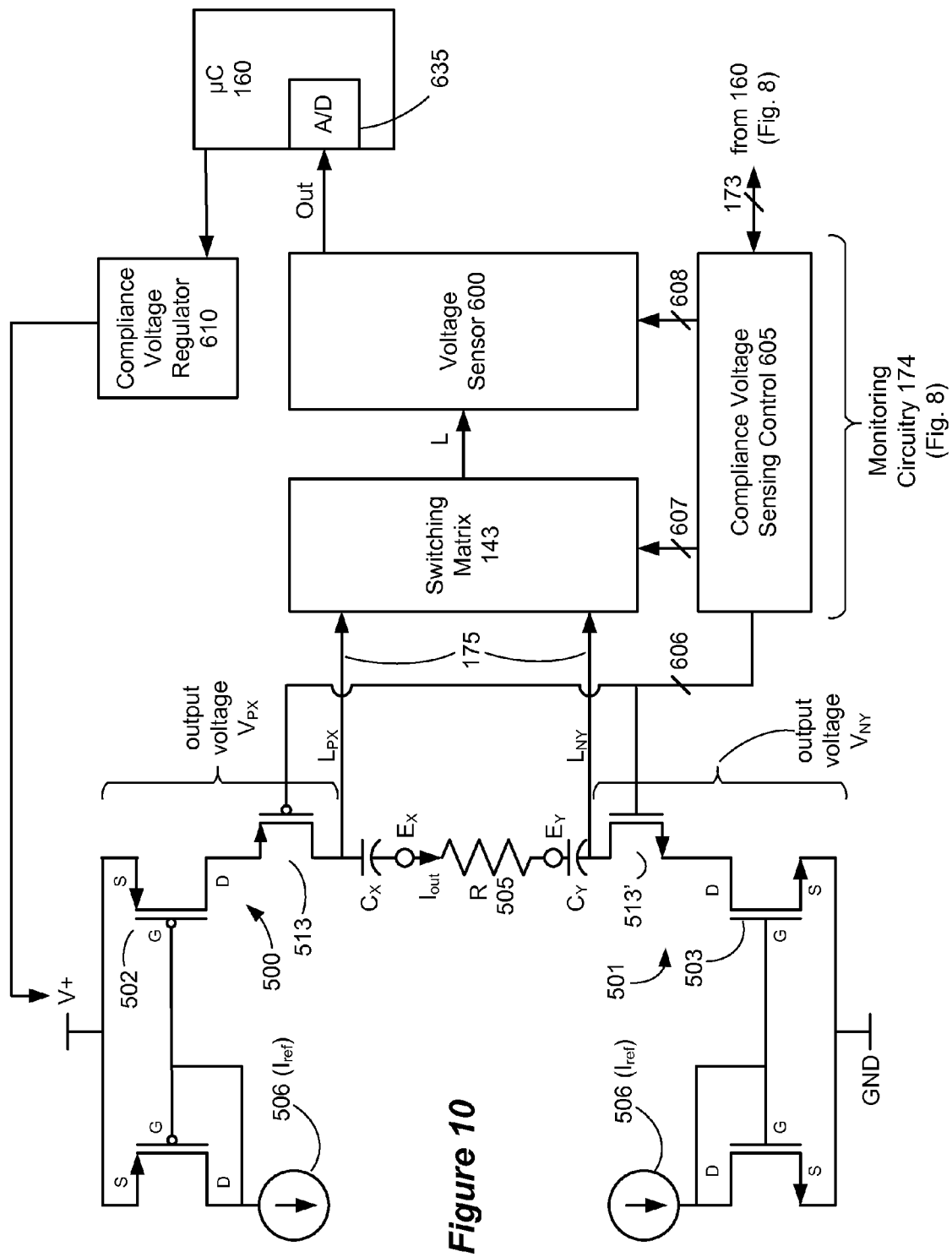
FIG. 10 shows an embodiment of circuitry usable in an implantable stimulator device for monitoring the output voltages across the current source and sink circuitry, and adjusting the compliance voltage accordingly, in accordance with an embodiment of the invention.

Should the measured voltages across the output of the PDAC or NDAC be outside of the guard band voltages, the compliance voltage, V+, is changed to attempt to bring such measured voltages within acceptable limits in accordance with an algorithm explained in further detail below. However, before discussing this algorithm, specifics of the circuitry used to measure the output voltages is discussed, starting with FIG. 10. For the most part, FIG. 10 illustrates further details of the monitoring circuitry 174 of FIG. 8, which comprises (in addition to other components) a compliance voltage sensing control circuit 605, a switching matrix 143, at least one voltage sensor 600, and a compliance voltage regulator 610. Feeding into this circuitry, and specifically into the switching matrix 143, are lines L 175 associated with each electrode. In a given architecture, more than one current source circuit or current sink circuit (e.g., current mirror) may contribute to the current at a particular electrode. However, for ease of illustration, only one source circuit 500 and sink circuit 501 are shown in FIG. 10 for simplicity.

Given the tap point of the lines L 175, the voltage present on the lines is indicative of the output voltage of the source and sink circuitry. As shown, this output voltage comprises the voltage drop across both the output transistors of the source and sink circuitry 502, 503 (which as noted earlier, can comprise a plurality of paralleled transistors to scale current gain), and across the selection transistors 513, 513' used to select those output transistors as contributing to the current. In other embodiments, the lines could be placed between the output transistors 502 and 503 and the selection transistors 513, 513', although this is not considered as beneficial because it would exclude from monitoring realistic voltage drops occurring across the selection transistors 513, 513'. The lines 175 are used in the sensing of the output voltage. The output voltage across current sink (NDAC) 501 at electrode $E_Y$ comprises the absolute voltage on line $L_{NY}$, which does require a difference calculation as the NDAC is referenced to ground. By contrast, the output voltage across the current source (PDAC) 500 at electrode $E_X$ comprises the difference between the compliance voltage, V+, and the voltage measured at line $L_{PX}$.

The voltages for the lines 175 are provided to a switching matrix 143. As noted above, while only two lines 175 are shown for ease of illustration in FIG. 10, many more lines would be present, depending on the number of electrodes present. In one embodiment, the switching matrix 143 is used to select the voltage on one line, and to present that voltage (L) to voltage sensor 600. As can be seen, the selection transistors 513, 513', the switching matrix 143, and the voltage sensor 600 are all controlled by a compliance voltage sensing control circuitry 605 via busses 606, 607, and 608. Ultimately, the compliance voltage sensing circuit 605 receives signals from the microcontroller 160 (FIG. 8), which informs the control circuitry 174 when and how the various measurements are to be made consistent with the disclosed algorithm, as explained in further detail below.

The voltage sensor 600, in one embodiment, outputs an analog voltage, "Out," to the microcontroller 160, which as shown contains an analog-to-digital (A/D) interface 635. This allows the microcontroller 160 to understand and digitally process the output voltage, and in accordance with the disclosed algorithm to send control signals to the compliance voltage regulators 610, i.e., the circuitry that ultimately adjusts the compliance voltage, V+.

As noted earlier, it is preferable in a current-mirror based source or sink circuit that the output transistors 502, 503 operate in saturation, but not excessively so, lest power is needlessly lost. Accordingly, embodiments of the invention seek to adjust the compliance voltage to keep the output transistors in active current sources and sinks in saturation. This may not always be possible, recognizing that the current source and current sink circuitry are serially connected through the load and hence act to "balance" one another, consistent with their current-voltage characteristics. If perfect saturation performance cannot be achieved in both the source and the sink, the compliance voltage will be set to as logical a value as possible to ensure proper circuit performance with minimal power loss.

FIG. 12 shows the current-voltage characteristics for the output transistors 502, 503 viewed in isolation. (More accurately, the I-V curve for the N-channel output transistors 503 in the sinks 501 is shown; one skilled will understand that the P-channel output transistors 502 in the sources would have opposite polarity as is typical in CMOS circuit design). The I-V curve exhibits a saturation voltage, Vsat, above which the drain-to-source voltage, Vds, is sufficient to cause the transistor to operate in saturation. In a preferred embodiment, it is desired that the output transistors 502, 503 operate within a guard band range of voltage as shown. While the lower limit of the guard band could comprise Vsat, it is preferred to choose a slightly elevated lower range value to allow for margin and to account for the normally-small voltage drop across the selection transistors 513, 513' which may also be included in the monitored output voltages. The upper limit of the guard band voltage is chosen not to be excessive, and demarks a limit within the output transistors are in saturation, but not excessively so. In preferred embodiments, the guard band voltage for current sources (PDACs) ranges from 1.5V to 2.1V, while the guard band voltage for current sinks (NDACs) ranges from 1.2V to 1.8V. (The lower values for the NDAC reflect that the N-channel output transistors 503 would normally have slightly lower saturation voltages than would comparable P-channel output transistors 502 in the PDAC).

Figure 2A:
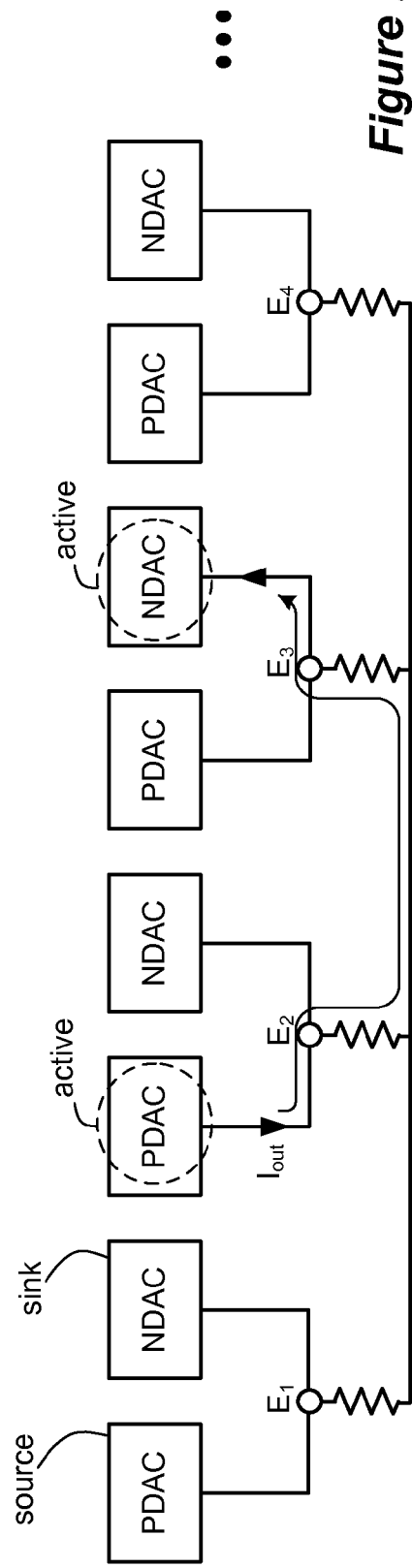
FIGS. 2A-2B shows a prior art architecture for coupling output current sources and sinks to a plurality of electrodes using hard-wired dedicated circuitry at each electrode.
Figure 2B:
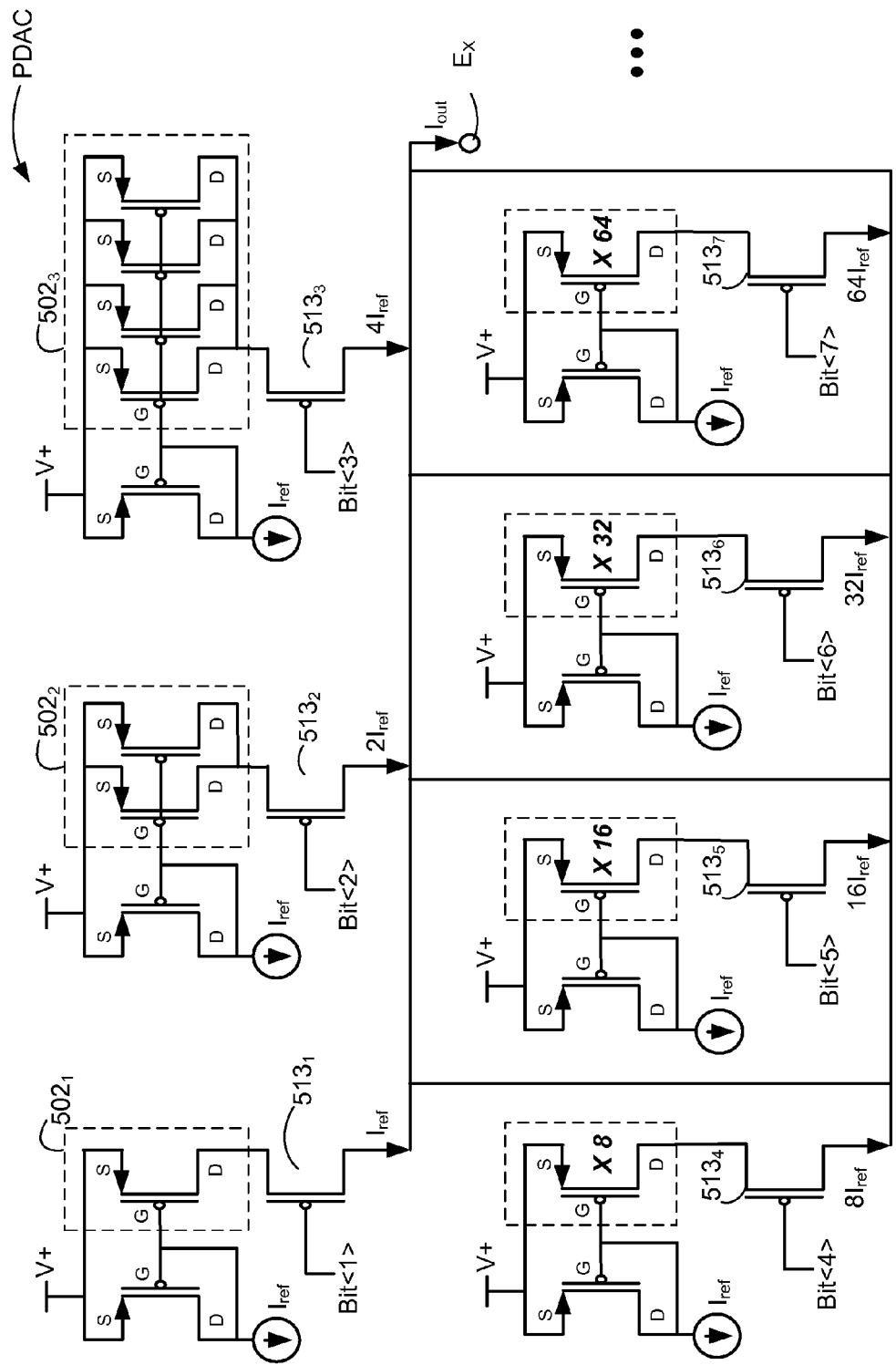
Figure 3A:
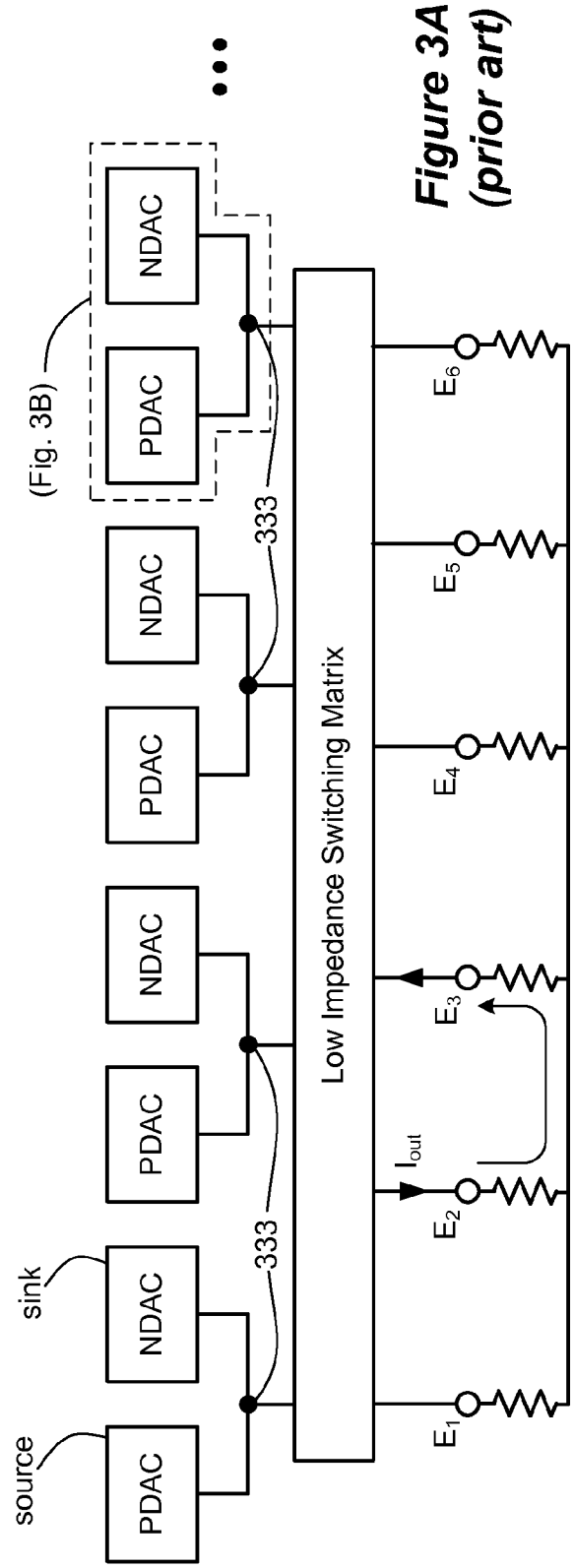
Figure 4A:
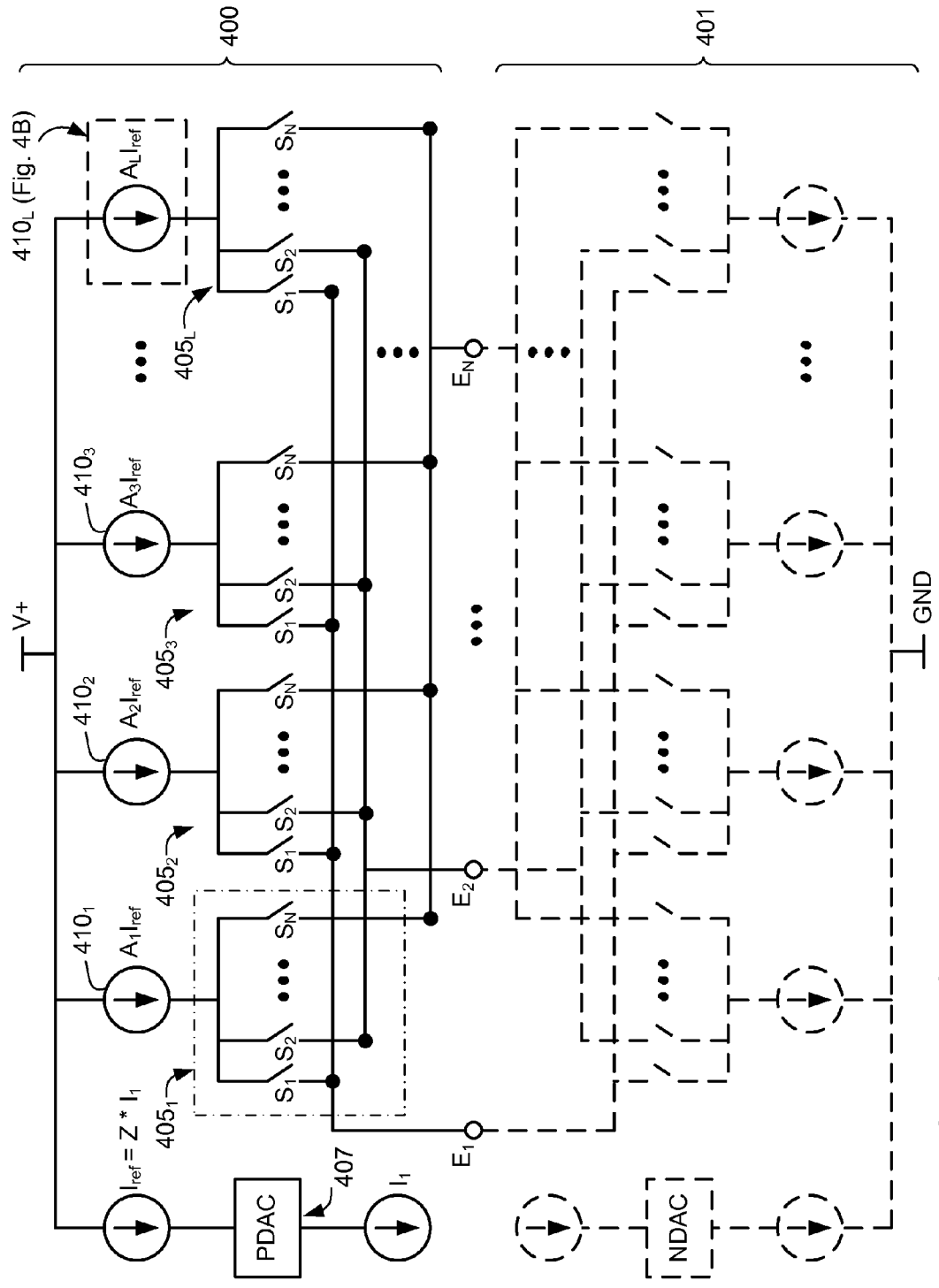
FIGS. 4A-4C shows a prior art architecture for sourcing a sinking current to a plurality of electrodes using distributed current source and current sink circuitry.
Figure 4B:
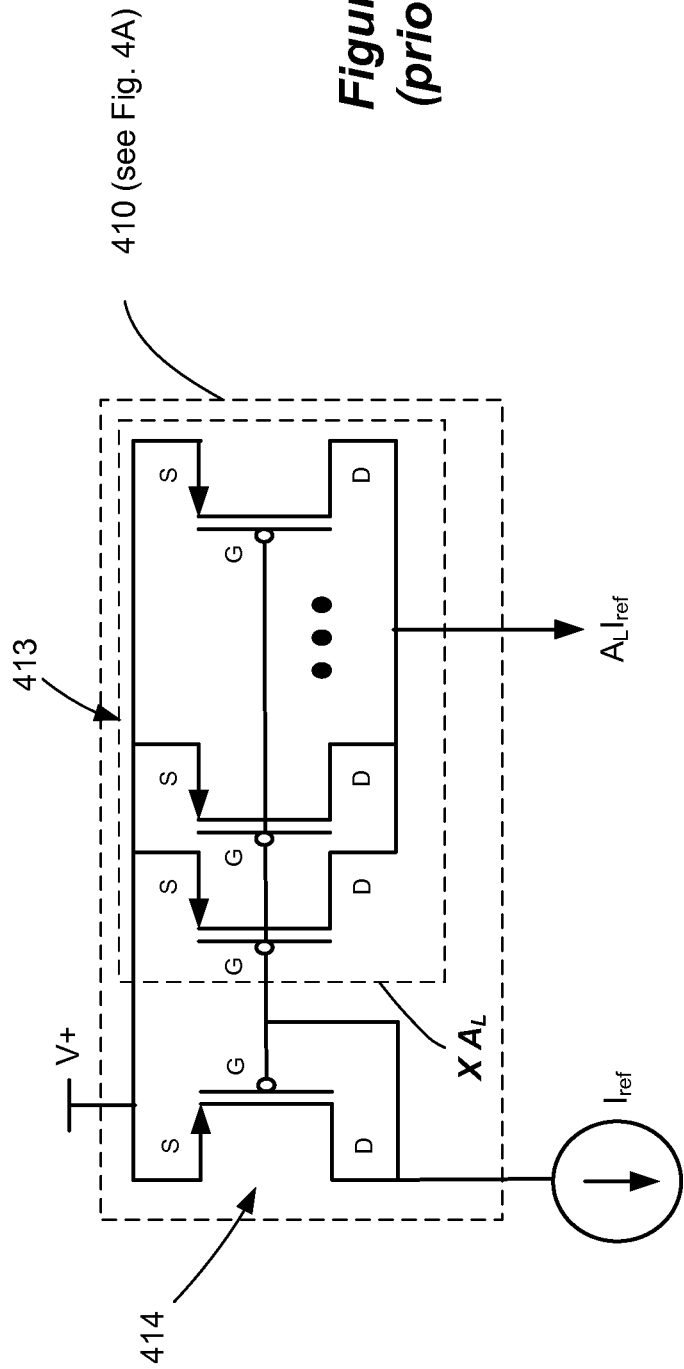
Figure 4C:
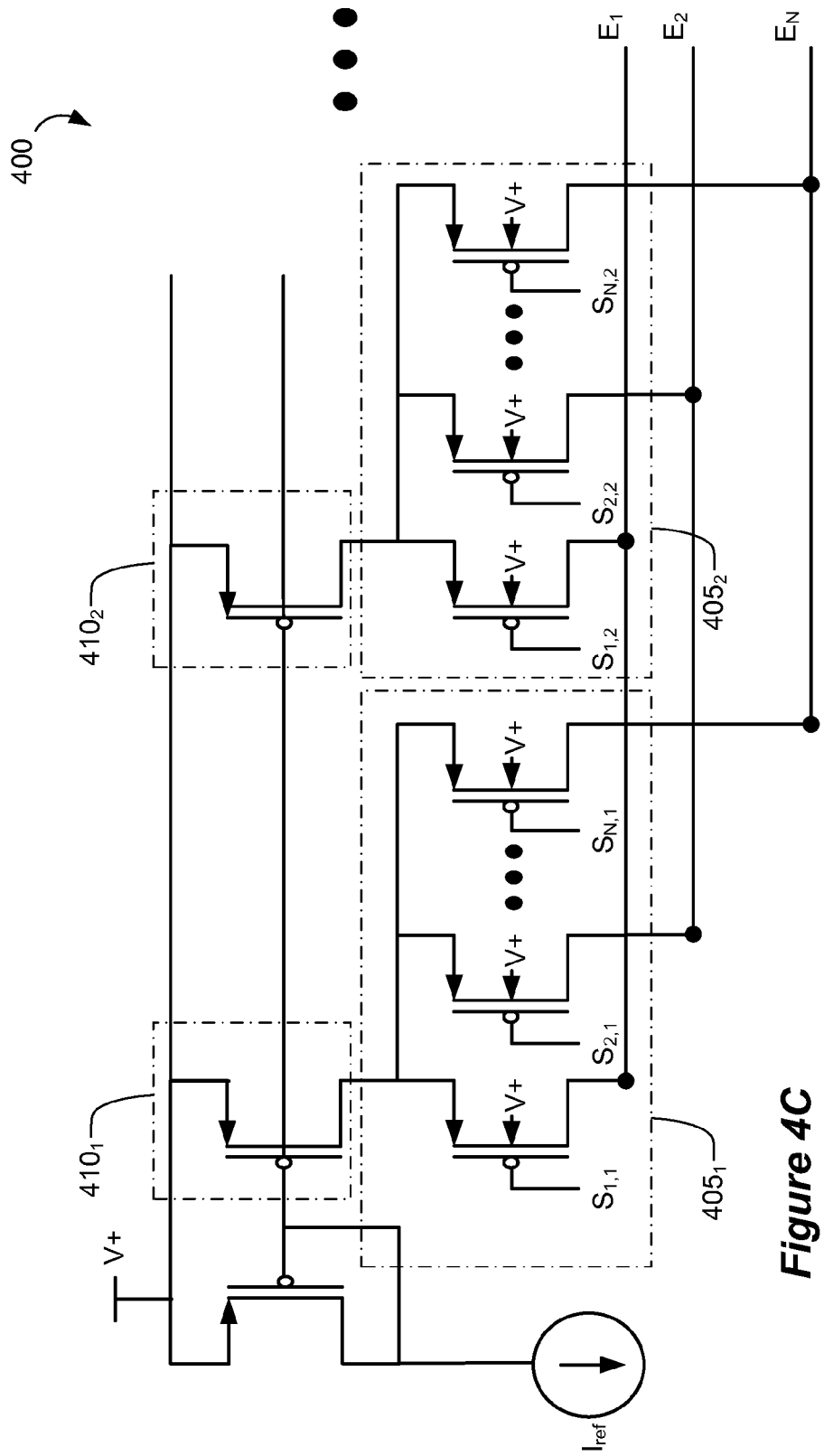
Figure 14:
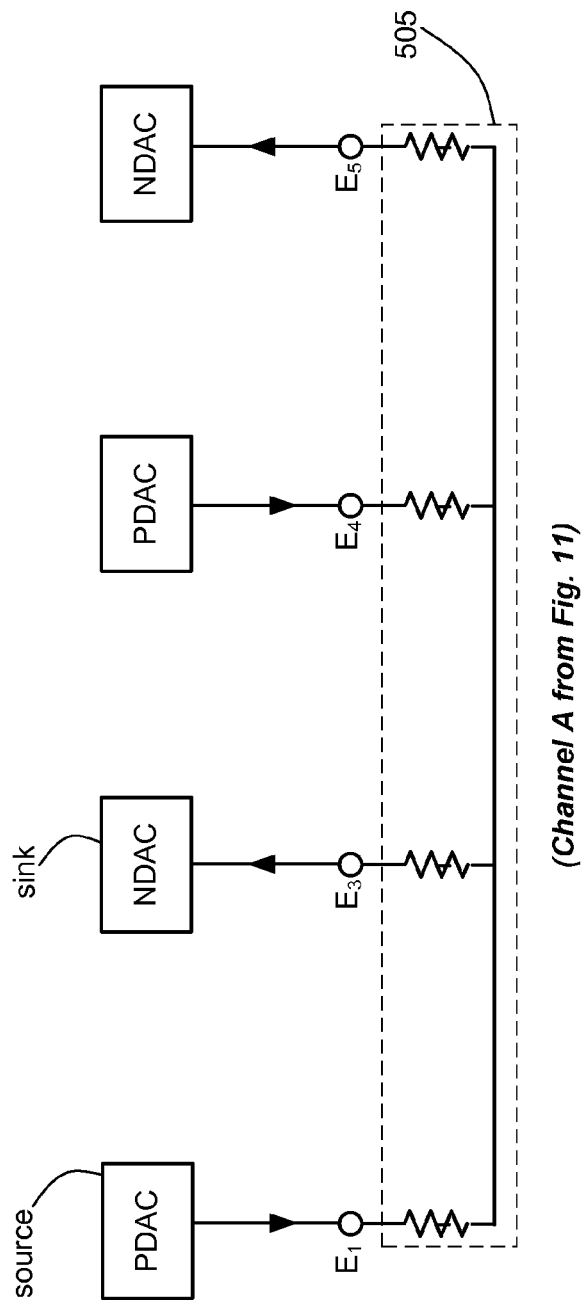
FIG. 14 shows the active current sources and sinks for an exemplary timing channel and the resistive network (i.e., load) which such circuitry stimulates.
Figures 16A, 16B:
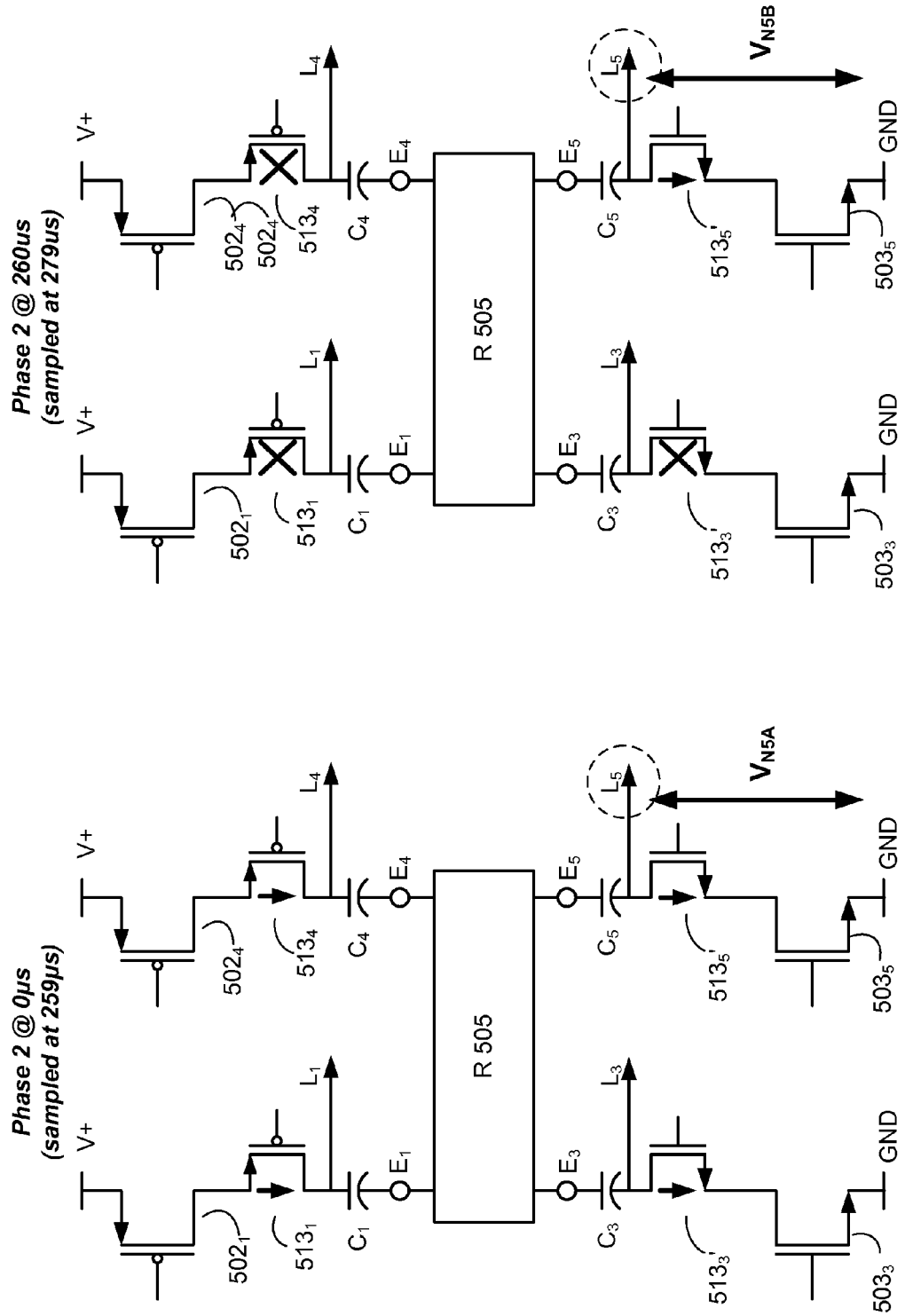
Figure 17B:
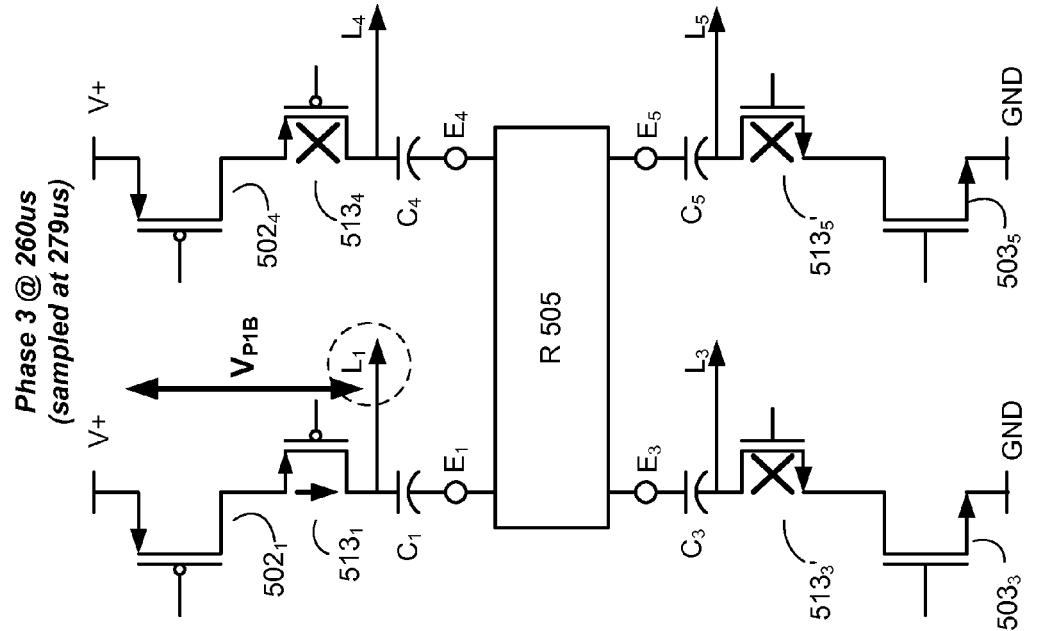
Figure 17A:
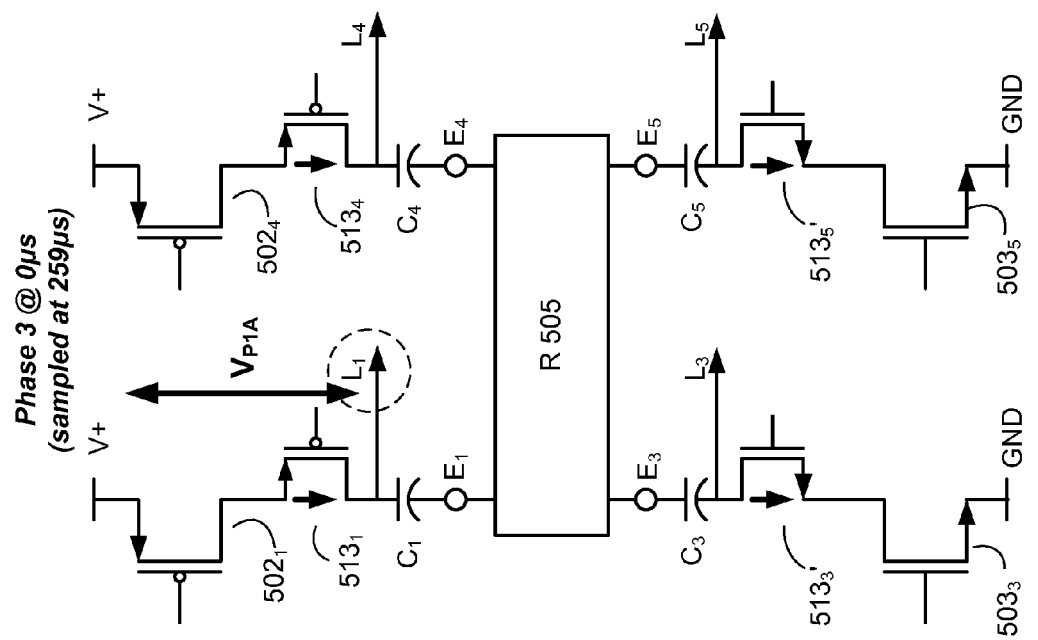
Figure 18B:
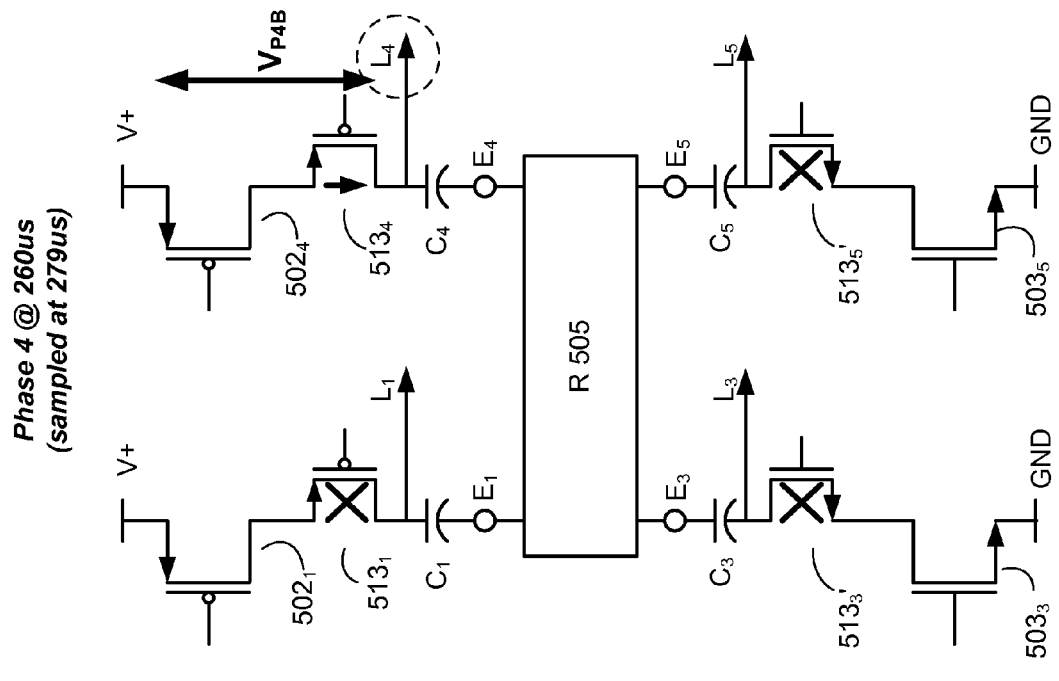
Figure 18A:
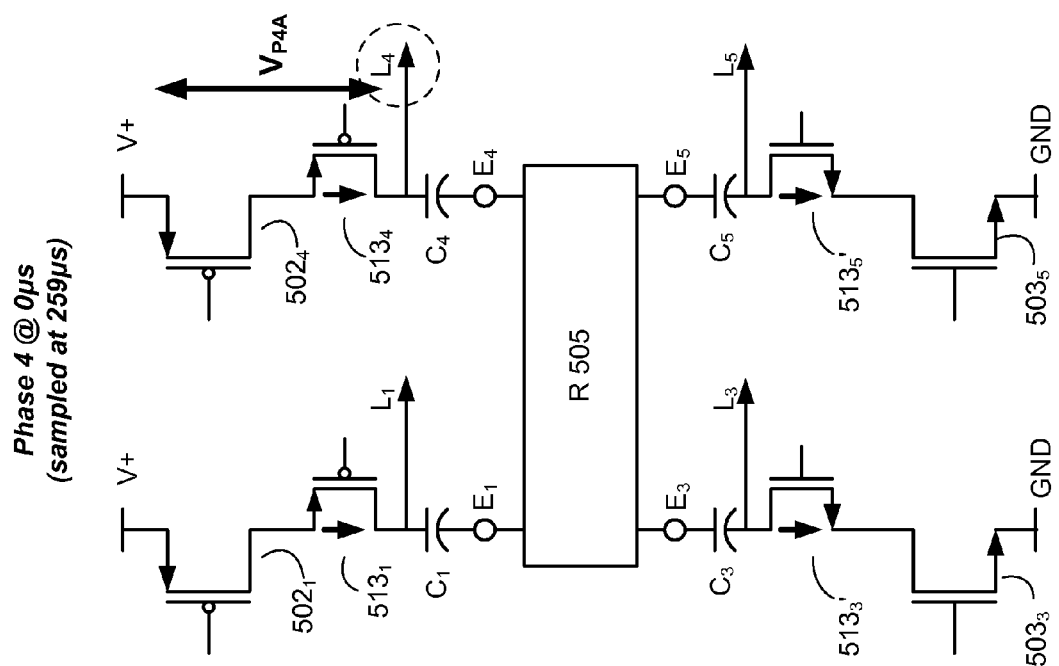

As discussed earlier, FIG. 11 shows various timing channels usable by an IPG 100, and specifies which device electrodes are to act as current sources and sinks at a particular time. Timing channel A is used to illustrate an embodiment of the invention for compliance voltage adjustment. As can be seen, in channel A, two electrodes act as sources ($E_1$ and $E_4$), while two electrodes act as sinks ($E_3$ and $E_5$). As discussed earlier, more or less electrodes can act as sources or sinks of current, although only two of each are illustrated in exemplary timing channel A. So configured, the representative circuit, including the resistive network 505 constituting the patient's tissue, is shown in FIG. 14 for channel A. As one will appreciate, the various sources 500 and sinks 501 can be comprised of PDAC or NDAC circuitry dedicated to a particular electrode within the IPG 100 (e.g., FIGS. 2A and 2B), or could comprise other architectures as discussed earlier (e.g., FIGS. 3A to 4C).

Further details of this exemplary timing channel configuration, and the measurements made to monitor and ultimately adjust the compliance voltage V+, and shown with respect to FIGS. 15A-18B. Note in any one of these Figures that the output transistors 502, 503, the selection transistors 513, 513', the resistive network 505, and the lines L associated with each electrode, are shown. FIGS. 15A, 16A, 17A, and 18A represent the configuration of the source (PDAC) and sink (NDAC) circuitry during the delivery of actual stimulation pulses to the patient as prescribed by timing channel A and other specifics of stimulation (e.g., pulse width, amplitude, frequency, etc.). Thus, note in these Figures that all PDACS and NDACs are connected to the circuit, i.e., the selection transistors 513, 513' are all on, as designated by the arrow with each transistor. Note also that in each of FIGS. 15A, 16A, 17A and 18A that the output voltage of the NDAC or PDAC circuitry at each electrode ($V_{N3A}$, $V_{N5A}$, $V_{P1A}$, $V_{P4A}$) is monitored via its corresponding line ($L_3$, $L_5$, $L_1$, $L_4$), starting first with the NDACs (lines $L_3$, $L_5$) followed by the PDACs (lines $L_1$, $L_4$).

As shown, each of these output voltages ($V_{N3A}$, $V_{N5A}$, $V_{P1A}$, $V_{P4A}$) are monitored in series, with $L_3$'s output voltage being measured during a first stimulation phase, $L_5$'s output being measured during a second stimulation phase, etc. However, while serial monitoring is a necessity in embodiments having only a single voltage sensor 600 (FIG. 10), it should be noted that these output voltages can also be monitored in parallel. Thus, if it is assumed that four PDACs can act as current sources and four NDACs can act as current sinks during one timing channel, then eight voltage sensors 600 (not shown) would allow for simultaneous sensing of all voltages. In such a case, bus 607 would enable the switching matrix 143 to simultaneously pass these eight voltages to the eight different voltage sensors 600.

Figure 13:
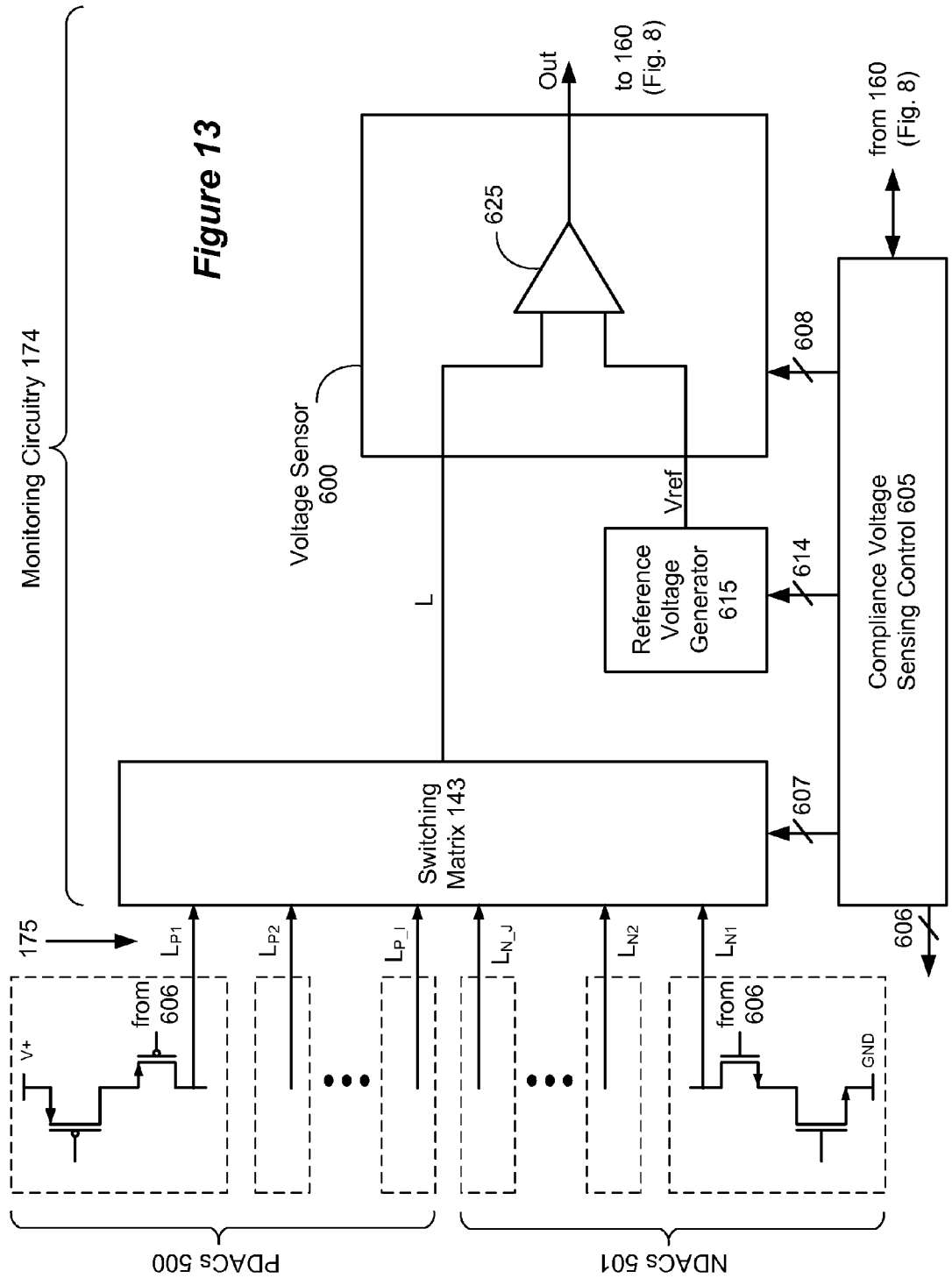
FIG. 13 shows further details of the circuitry of FIG. 10.

In any event, and as noted earlier, these NDAC and PDAC output voltages as tapped by lines 175 are passed via the switching matrix 143 to the voltage sensor 600, for which further details are shown in FIG. 13. In a preferred embodiment, the voltage on any particular chosen line L is deduced by sending that voltage to a difference amplifier 625. As is common with such difference amplifiers, a reference voltage Vref is also input. Reference voltage Vref is maintained by reference voltage generator 615, which may comprise a 1.2V band gap reference circuit for example. Reference voltage generator 615 is controlled by bus 614 passed from compliance control 605 to allow an appropriate reference voltage to be generated with a proper value and at an appropriate time.

Ultimately, the differential voltage (Out; FIGS. 10, 13) is sent to the A/D interface 635 of the microcontroller 160. In this regard, signal "Out" may be a relative value representative of the output voltages across the NDACs and PDACs, but may not comprise the actual value of those output voltages. Instead, the actual value of the output voltage drops may be computed in the microcontroller 160, which for example may derive the actual output voltages by subtracting out the effects of the reference voltage, Vref; by comparing such voltages to the currently-set compliance voltage, V+, etc. In other words, signal "Out" needs merely to inform the microcontroller 160 of a value from which the microcontroller can deduce the output voltage across the current source and sink circuitry. Of course, output voltage sensing can occur in many different ways, and as one skilled in the art will appreciate. For example, although in a preferred embodiment sensing occurs relative to a reference voltage, Vref, sensing could also occur relative to the compliance voltage, V+, ground, or any other voltage. In short, what is important is that the output voltages on the lines L 175 be sensed; the way in which this specifically occurs is not important.

Figure 19:
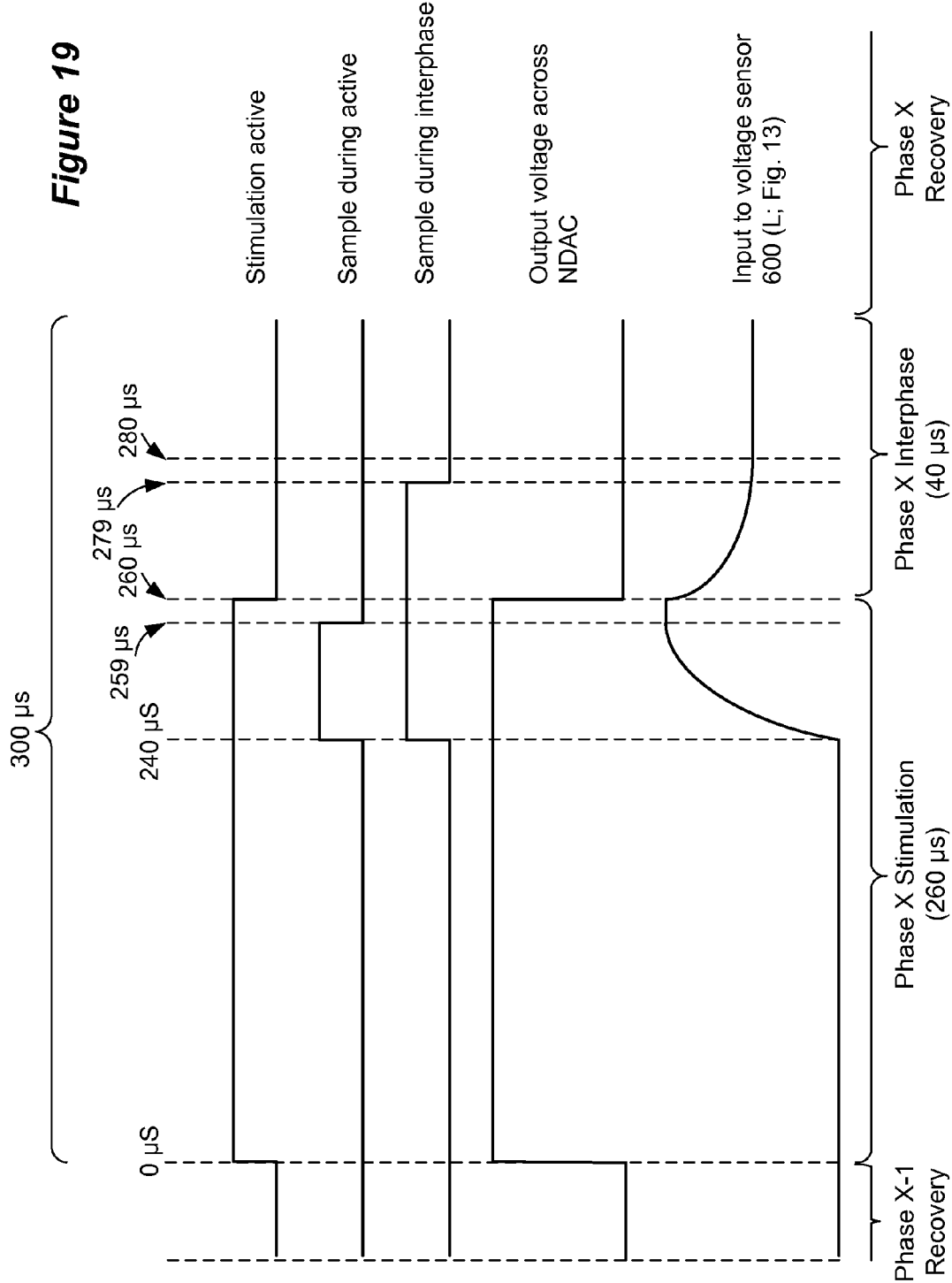
FIGS. 19 and 20 respectively show exemplary timing signals indicative of the operation of the compliance voltage monitoring circuitry of FIGS. 10 and 13 for the active current sinks (NDACs) and current sources (PDACs).
Figure 20:
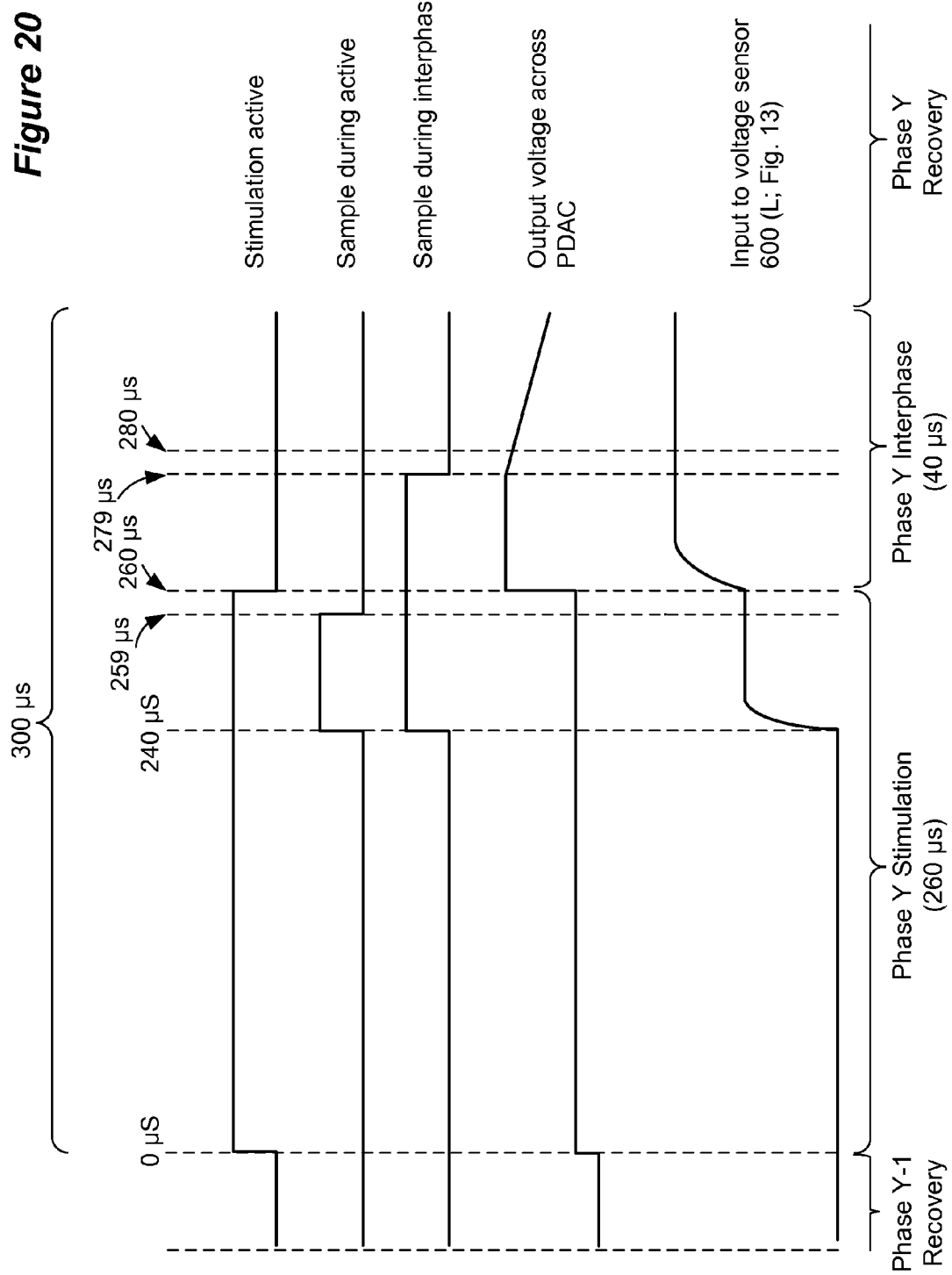

FIGS. 19 and 20 respectively show an embodiment of how these output voltages can be deduced for both the NDACs (FIG. 19) and the PDACs (FIG. 20). In both Figures, the three top traces represent signals indicative of the operation of the IPG and of the compliance voltage sensing circuitry. The first signal indicates when active stimulation is occurring in the IPG 100. As shown in this example, that period is 260 microseconds, but this length can vary depending on the frequency and duration of the stimulation pulses specified for a given patient's therapy, as explained further below. After the active stimulation phase, i.e., starting at 260 microseconds, the IPG enters an "interphase" period during which no stimulation occurs. (The interphase period, and how it can be used in voltage monitoring and compliance voltage adjustment, will be explained in further detail later).

The second trace shown in FIGS. 19 and 20 comprises a control signal which dictates when the output voltages are monitored during the active stimulation phase. This second trace signal, called "sample during active," would comprise one or more control signals sent by the compliance voltage sensing control circuitry 605 (see FIGS. 10 and 13). As shown, the sample during active signal comprises a set up/sample signal. Specifically, on the rising edge, the output voltage is permitted to pass to the voltage sensor 600, for example, by allow the voltages on lines 175 to pass through the switching matrix 143 (see FIGS. 10 and 13). The falling edge of the sample during active signal, by contrast, actually sampled the output voltage at the voltage sensor 600. In the particular embodiment illustrated, this type of set up/sample scheme is beneficial to allow the output voltages to settle and ramp to appropriate levels This is necessary when considering the settling time and capacitance of the voltage sensing circuit, as discussed further below. Such voltage settling can be seen in the fourth and fifth traces, which respectively show the output voltage across the NDAC (FIG. 19) and PDAC (FIG. 20), and those voltages as input to the voltage sensor 600. As can be seen, by allowing the passed voltages to stabilize, they can be sampled at reliable, stable values.

In the embodiment shown in FIGS. 19 and 20, set up and sampling occur towards the end of the active stimulation period, i.e., at 240 and 259 microseconds respectively. Set up and sampling is beneficial towards the end of the stimulation pulse, again, to allow for settling and stabilization of the circuitry during stimulation. For example, the coupling capacitors, Cx, charge up during the active stimulation period, such that the voltage across them is the largest at the end of the active stimulation pulse. Therefore, it is preferable for sampling to occur towards the end of the active stimulation period, as this allows compliance voltage sensing to account for any such coupling capacitor voltages. Moreover, because the compliance voltage V+ might droop during active stimulation, sampling near the end of active stimulation is further beneficial as this will consider such a droop when it is at its maximum. Additionally, sensing near the end of stimulation also allows polarization voltage build-up on the electrode-tissue interface to be accounted for.

Of course, set up and sampling of the output voltages across the NDACs and PDACs can occur in many different way, and will be implementation specific. Thus, just as the voltage sensor 600 can be implemented in several different ways, sampling of the voltage too will depend on the implementation used. In short, the sampling and control signals as shown in FIGS. 19 and 20 should be understood as merely exemplary of one embodiment. Again, the important issue is that the output voltage across the NDACs and PDACs be monitored at logical times so these values can be passed to and processed by the compliance voltage adjustment algorithm to be discussed shortly.

Before discussing this algorithm, an alternative embodiment for measuring the output voltage across the NDACs and PDACs is discussed. In this variation, not only is the output voltage during stimulation measured, but the output voltage during periods of no stimulation is measured as well. Specifically, in a preferred embodiment, the output voltage is measured during the interphase period, i.e., during a period between active stimulation pulses. Such measurements are shown in FIGS. 15B, 16B, 17B, and 18B. As seen in those Figures, the voltage on the line of interest for each active NDAC and PDAC in a given timing channel is monitored while all other DACs are disconnected. For example, in FIG. 15B, the voltage across the first NDAC, corresponding to electrode $E_3$, is measured ($V_{N3B}$), and thus its selection transistor, 513$_3$', is on. By contrast, all other DACs are off, i.e., selection transistors 513$_1$, 513$_4$, and 513$_5$' are off. As a result, no or minimal current will flow through the resistive network 505 comprising the patient's flesh, as the pathway between the compliance voltage, V+, and ground is interrupted. However, even though the NDAC at electrode $E_3$ is disconnected from the compliance voltage, V+, some residual output voltage may be present on line $L_3$ by virtue of that NDAC otherwise being on.

This interphase output voltage measurement can be used to improve the accuracy of the output voltage as processed by the microcontroller 160, and ultimately as considered by the compliance voltage adjustment algorithm. Preferably, the interphase output voltage measurement (again, generally negligible but potentially significant in value) is subtracted from the active stimulation measurement at any particular DAC. Thus, notice in FIGS. 15A and 15B that active (A) and interphase (B) measurements are made at electrode $E_3$, which are designated as $V_{N3A}$ and $V_{N3B}$, and likewise for the other DACs in FIGS. 16, 17 and 18. The result in this example is eight output voltage measurements: $V_{N3A}$, $V_{N5A}$, $V_{P1A}$, $V_{P4A}$ for the active measurements, and $V_{N3B}$, $V_{N5B}$, $V_{P1B}$, $V_{P4B}$ for the interphase measurements.

To improve the accuracy of the output voltages for the DACs to be processed by the compliance voltage adjustment algorithm, these output active and interphase measurements are preferably subtracted for each DAC. Thus, in a preferred embodiment, the output voltage across the DAC at electrode $E_3$ to be sent to the compliance adjustment voltage algorithm would comprise $V_{N3A}$-$V_{N3B}$. By doing this, assessment of the operating region (saturation) of the output transistors in the DAC can be improved, as residual voltages due to the active DAC itself, as well as voltage drops resulting from the selection transistors 513, 513' can be corrected out of the output voltage measurement.

Taking of the interphase output voltage measurement is shown with reference once again to FIGS. 19 and 20. Specifically, the third trace, called "sample during interphase," comprises a control signal which dictates when the output voltages are monitored during the interphase period. This third control signal is similar to the second control signal (sample during active) discussed earlier, and comprises a set up/sample signal. Specifically, after set up, the falling edge actually samples the input to the voltage sensor, which again requires some time to stabilize from its active value. In the example shown in FIGS. 19 and 20, such sampling occurs at 279 microseconds, i.e., 19 microseconds into the interphase period, but again these times and sensing schemes can vary and are implementation dependent. The important issue, should an interphase measurement be used to supplement the active measurement, is to take the measurement at a sensible time consistent with the implementation chosen, and this can occur in different ways and with different timings.

It should be noted while the monitoring of the interphase output voltages can be beneficial for the reasons just explained, the use of such interphase measurements is not required in all useful embodiments. Instead, only the active phase measurements (i.e., those illustrated in FIGS. 15A, 16A, 17A, and 18A) can be used. As previously noted, those active output voltage measurements can be made simultaneously. By contrast, should interphase measurements be made t measure the inactive output voltage across each DAC, such measurements would need to be made serially, i.e., during sequential interphase periods.

In a preferred embodiment, the output voltage measurements for each active electrode specified within a particular timing channel is taken sequentially, and in the order specified in FIGS. 15A-18B. Thus, the sinking electrodes are measured first: thus the NDAC circuitry associated with electrode $E_3$ is measured first during active stimulation (FIG. 15A), followed by the interphase (inactive) measurement for $E_3$ (FIG. 15B), followed later by the same measurements for $E_5$ (FIGS. 16A & B), etc. The compliance voltage can then be adjusted as specified with respect to FIG. 21 below. Then, the sourcing electrodes are similarly measured in series (FIG. 17A-18B).

Because the measurements are made in the context of actual prescribed therapy, the timing of the monitoring signals is preferably adjustable. In this regard, it is particularly important to consider the frequency and duration of the prescribed stimulation pulses so that the set up/sample measurements are properly "fit" to the stimulation pulses and to the interphase periods between them. For example, while the timing of the signals for the example shown in FIGS. 19 and 20 would be appropriate for one frequency, a higher frequency would require tighter timing.

Moreover, between each stimulation pulse, and as is common in implantable stimulators, a charge recovery phase may follow. As is known, such a recovery period could comprise pulsing to recover the charge passed into the load, i.e., the tissue 505. Usually, such recovery is biphasic, and is implemented by recovery pulses of equal magnitude and duration to the active pulses but of opposite polarity. Charge recovery can also be accomplished passively, as is well known. Such charge recovery is not shown in the Figures for simplicity, but would be a consideration in an embodiment of the invention. Moreover, it should be noted that DAC output voltages can be measured during charge recovery, but again this is not further discussed for simplicity.

Figure 21:
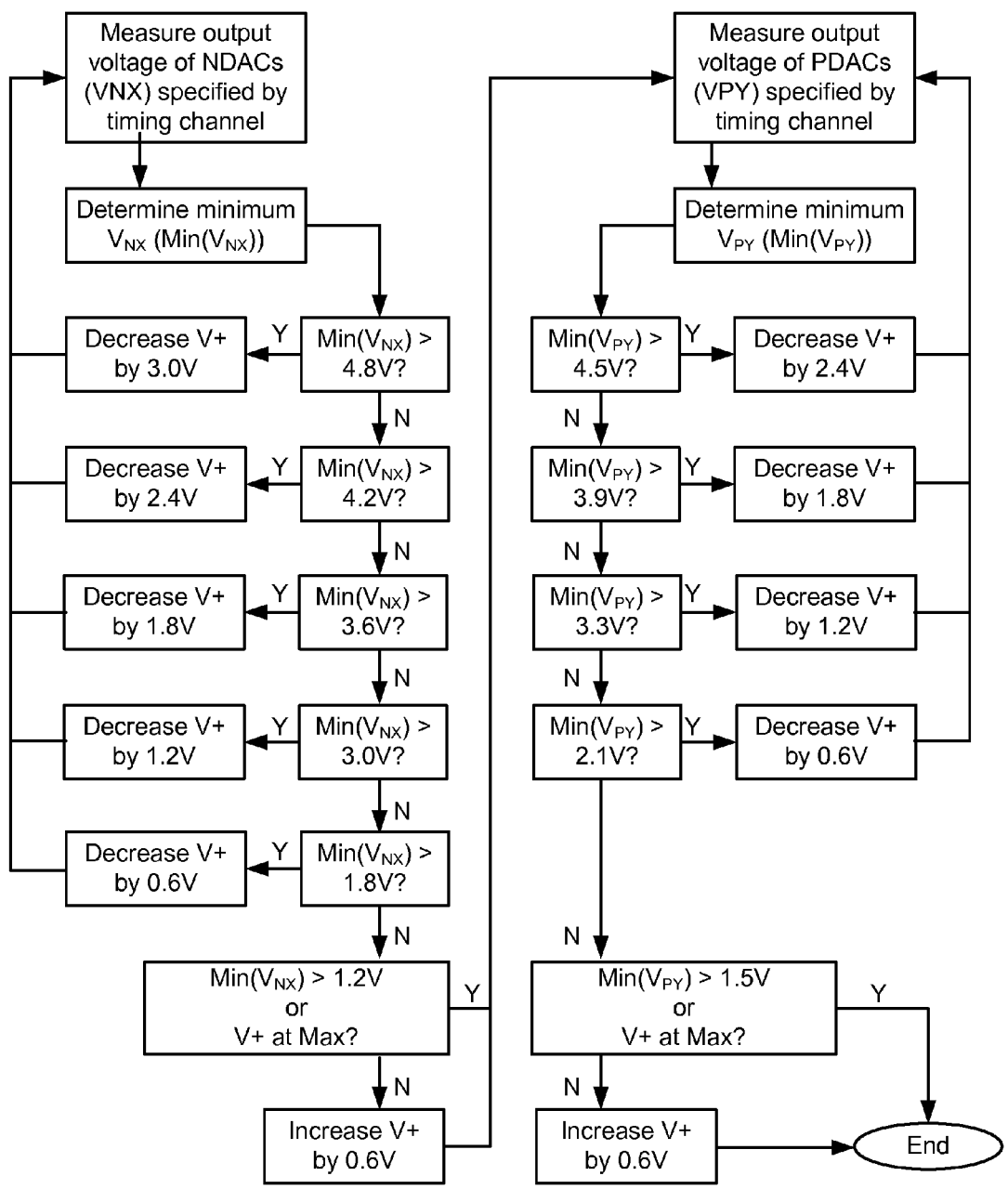
FIG. 21 shows a flow chart illustrating an exemplary algorithm for monitoring and adjusting the compliance voltage in accordance with an embodiment of the invention.

Now that the various means for monitoring the output voltage of the DACs has been described, attention turns to how, algorithmically, those voltages are used to adjust the compliance voltage to an efficient level. As shown in FIG. 21, the algorithm starts by first acquiring all relevant output voltages for the NDACs ($V_{N1}$, $V_{N2}$, ... $V_{NX}$) for a given timing channel as just described. It should be understood that these output voltages can comprise only the measurements taken during active stimulation (e.g., $V_{N3A}$ from FIG. 15A), or the voltage computed as the difference between the active and interphase measurements (e.g., $V_{N3A}$-$V_{N3B}$ from FIGS. 15A and 15B). Normally, the algorithm would start with the compliance voltage, V+ at its maximum value (e.g., 16.8V), but could start at a lesser value.

Next, the minimum output voltage for the NDACs (Min ($V_{NX}$)) is determined. This minimum output voltage would suggest the NDAC most at risk to be in sub-saturation, and hence in this embodiment of the algorithm is considered the most efficient to track. Accordingly, the algorithm next asks how that minimum value compares relative to the range of guard band voltages for the NDACs. Essentially, if Min($V_{NX}$) is higher than the maximum guard band voltage for the NDACs (e.g., 1.8V), the compliance voltage V+ is decreased, because it can be inferred that all NDACs are at this point operating with output voltages that are too high to be optimal from a power consumption standpoint. As shown, to expedite the iterative nature of the algorithm, the extent to which the compliance voltage V+ is decreased scales with the extent to which Min($V_{NX}$) exceeds the upper guard band voltage for the NDACs. Thus, if Min($V_{NX}$) is very high above the guard band (e.g., Min($V_{NX}$)>4.8V) the compliance voltage is decreased by a large amount (e.g., 3.0V), but if barely above the guard band (1.8V<Min($V_{NX}$)<2.4V) the compliance voltage is decreased by a small amount (e.g., 0.6V).

Eventually, as the compliance voltage V+ is decreased, the minimum voltage drop across the NDACs, Min($V_{NX}$), will be within the guard band range (e.g., between 1.2V and 1.8V), and the PDACs can then be assessed. However, should Min ($V_{NX}$) fall below the minimum guard band voltage (e.g., 1.2V), the compliance voltage can be increased by an increment (e.g., 0.6V prior to assessment of the PDACs. Of course, if the compliance voltage is at maximum at this point, further increasing the compliance voltage will not be possible, and assessment of the PDACs will commence.

With the compliance voltage V+ adjusted at this point with respect to the NDACs, the algorithm then acquires all relevant output voltages for the PDACs ($V_{P1}, V_{P2}, \ldots V_{PY}$). Again, the minimum voltage drop across the PDACs, $Min(V_{PY})$ is determined, and the algorithm then proceeds as with the NDACs. Specifically, if $Min(V_{PY})$ is above the maximum guard band voltages for the PDACS (e.g., 2.1V), the compliance voltage is decreased, again by an amount commensurate with the deviation from the maximum guard band voltage.

Note that it is permissible to further decrease the compliance voltage at this point in the algorithm, even if some of the voltage drops across the NDAC were close to the minimum guard band voltage. Thus, V+ can be decreased if $Min(V_{PY})$ is above 2.1V for example, even when $Min(V_{NX})$ is below 1.8V and otherwise is optimal. While this would seem to run the risk of adjusting the NDACs out of alignment, note that $Min(V_{NX})$ is tied to (i.e., balanced with) $Min(V_{PY})$ by virtue of the current-voltage characteristics of both DACs. Because the currents must match for the NDACs and the PDACs, it is difficult to decrease $Min(V_{NX})$ significantly below the minimum NDAC guard band threshold (e.g., 1.2V) without also bringing $Min(V_{PY})$ below the minimum PDAC guard band voltage (e.g., 1.5V) and vice versa. Hence, due to this balancing between the NDACs and the PDACs, the compliance voltage can be reduced without significant risk of impacting circuit performance, i.e., such that the circuitry is unable to produce an optimal current.

Eventually, as the compliance voltage is decreased, should the minimum output voltage across a PDAC be within the guard band for the PDACs ($1.5 < Min(V_{PY}) < 2.1$, the compliance voltage is deemed optimal. Otherwise, should a PDAC be below the guard band at this point, the compliance voltage can be increased by an increment (0.6V).

Thus, through the use of this exemplary algorithm, the compliance voltage can be adjusted to an optimal value that is sufficient high to allow for proper circuit performance (i.e., sufficient current output), but low enough that power is not needlessly wasted via excessive voltage drops across the current output circuitry. While the above specifies a single embodiment of an algorithm for such dual current source and sink optimization, other algorithms are possible, and are subject to a programmer's particular preference, keeping power drain consideration and risk in mind. In short, the disclosed compliance voltage algorithm is merely representative of a manner for simultaneously optimizing both the NDACs and the PDACs during actual stimulation.

It should be noted that while the measured output voltages across the source circuit and the sink circuit are used to adjust the compliance voltage in an attempt to bring both of the output voltages to a suitable level or levels, the technique can also be used to merely attempt to bring one of the output voltages to a suitable level (e.g., within a range, to a particular point, above or below a point, etc.). Thus, both output voltages can be measured, and in another embodiment, benefits are had by adjustment of the NDAC or PDAC output voltages alone, although of course it is preferable to adjust both voltages.

It should be understood that the direction in which current flows is a relative concept, and different conventions can be used to define whether currents flow to or from various sources. In this regard, arrows showing the directions of current flows in the Figures, references to current flowing to or form various circuit nodes, references to currents being sunk or sourced, etc., should all be understood as relatively and not in any limiting sense.

It should also be understood that reference to an "electrode" implantable adjacent to a tissue to be stimulated includes electrodes on the implantable stimulator device, or associated electrode leads, or any other structure for directly or indirectly stimulating tissue. "Electrode" can also comprise a case electrode such as disclosed herein.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method for adjusting a compliance voltage in a stimulator device, comprising:
    using at least one source circuit and at least one sink circuit to provide stimulation pulses to a load between at least two electrodes;
    during the stimulation pulses, determining at least one first voltage across the at least one source circuit and determining at least one second voltage across the at least one sink circuit; and
    using the determined first and second voltages to adjust the compliance voltage,
    wherein the compliance voltage is formed across the series connection of the at least one source circuit, the load, and the at least one sink circuit.

2. The method of claim 1, wherein the at least one first voltage and the at least one second voltage are not determined simultaneously.

3. The method of claim 1, wherein only the at least one first voltage is determined during a first of the stimulation pulses, and wherein only the at least one second voltage is determined during a second of the stimulation pulses.

4. The method of claim 1, wherein the first and second voltages are used to adjust the compliance voltage by comparing the first and second voltages to at least one threshold.

5. The method of claim 4, wherein there is a first threshold and a second threshold, and wherein the at least one first voltage is compared to the first threshold, and wherein the at least one second voltage is compared to the second threshold.

6. The method of claim 4, wherein the compliance voltage is adjusted to a lower value if either of the first or second voltages is higher than the at least one threshold.

7. The method of claim 6, wherein the at least one threshold is indicative of saturation of output transistors across which the first and second voltages are determined.

8. The method of claim 1, further comprising generating the compliance voltage from a battery within the stimulator device.

9. The method of claim 1, wherein using the first and second voltages to adjust the compliance voltage comprises:
    assessing the first and second voltages to determine whether they are within at least one guard band range of voltages; and
    adjusting the compliance voltage to bring the first and second voltages within the at least one guard band range of voltages.

10. The method of claim 9, wherein there is a first guard band range of voltages and a second guard band range of voltages, and wherein the at least one first voltage is assessed to determine whether they are within the first guard band range of voltages, and wherein the at least one second voltage is assessed to determine whether they are within the second guard band range of voltages.

11. The method of claim 9, wherein the compliance voltage is adjusted to a lower value if either of first or second voltages is higher than the at least one guard band range of voltages.

12. The method of claim 9, wherein the at least one guard band range of voltages is set in recognition of the saturation threshold of output transistors across which the first and second voltages are determined in the at least one source circuit and the at least one sink circuit.

13. The method of claim 1, further comprising, during interphase periods in which the stimulation pulses are not provided, determining at least one third voltage across the at least one source circuit and determining at least one fourth voltage across the at least one sink circuit.

14. The method of claim 13, further comprising using the using the first, second, third, and fourth voltages to adjust the compliance voltage.

15. A method for adjusting a compliance voltage in a stimulator device, comprising:
- using at least one source circuit and at least one sink circuit to provide a first stimulation pulse to a load between at least two electrodes;
- during the first stimulation pulse, determining at least one first voltage across the at least one source circuit;
- using the at least one source circuit and the at least one sink circuit to provide a second stimulation pulse to the load;
- during the second stimulation pulse, determining at least one second voltage across the at least one sink circuit; and
- using the at least one first voltage and the at least one second voltage to adjust the compliance voltage,
- wherein the compliance voltage is formed across the series connection of the at least one source circuit, the load, and the at least one sink circuit.

16. The method of claim 15, wherein the at least one first voltage and the at least one second voltage are used to adjust the compliance voltage by comparing them to at least one threshold.

17. The method of claim 16, wherein there is a first threshold and a second threshold, and wherein the at least one first voltage is compared to the first threshold, and wherein the at least one second voltage is compared to the second threshold.

18. The method of claim 15, further comprising generating the compliance voltage from a battery within the stimulator device.

19. The method of claim 15, wherein using the at least one first voltage and the at least one second voltage to adjust the compliance voltage comprises:
- assessing the at least one first voltage to determine whether they are within a first guard band range of voltages;
- assessing the at least one second voltage to determine whether they are within a second guard band range of voltages; and
- adjusting the compliance voltage to bring the at least one first voltage within the first guard band range of voltages and to bring the at least one second voltage within the second guard band range of voltages.

20. The method of claim 15, further comprising, during interphase periods in which neither the first or second stimulation pulses are provided, determining at least one third voltage across the at least one source circuit and determining at least one fourth voltage across the at least one sink circuit.

21. The method of claim 20, further comprising using the first, second, third and fourth voltages to adjust the compliance voltage.

\* \* \* \* \*